(12) United States Patent
Hofeldt

(10) Patent No.: US 9,560,960 B2
(45) Date of Patent: Feb. 7, 2017

(54) AMBLYOMETER FOR BALANCING BRIDGING RIVALROUS BINOCULAR VISION

(71) Applicant: Albert John Hofeldt, Miami Beach, FL (US)

(72) Inventor: Albert John Hofeldt, Miami Beach, FL (US)

(*) Notice: Subject to any disclaimer, the term of this patent is extended or adjusted under 35 U.S.C. 154(b) by 68 days.

(21) Appl. No.: 13/655,283

(22) Filed: Oct. 18, 2012

(65) Prior Publication Data

US 2013/0100400 A1     Apr. 25, 2013

Related U.S. Application Data

(60) Provisional application No. 61/627,815, filed on Oct. 19, 2011.

(51) Int. Cl.
*A61B 3/08*     (2006.01)
*A61B 3/02*     (2006.01)

(52) U.S. Cl.
CPC *A61B 3/08* (2013.01); *A61B 3/022* (2013.01)

(58) Field of Classification Search
CPC ......... A61B 3/08; A61B 3/103; A61B 3/1225; A61B 3/04; A61B 3/0285; A61B 3/032; A61B 3/1015; A61B 3/022
USPC ............... 351/200, 201, 203, 204, 215, 222, 233,351/234, 240, 243, 246
See application file for complete search history.

(56) References Cited

U.S. PATENT DOCUMENTS

| | | | | |
|---|---|---|---|---|
| 4,863,258 A | * | 9/1989 | Greene | 351/201 |
| 5,764,340 A | * | 6/1998 | Hofeldt | 351/201 |
| 6,851,807 B2 | * | 2/2005 | Holdeman | 351/203 |
| 7,690,790 B2 | * | 4/2010 | Hosoi et al. | 351/242 |

* cited by examiner

*Primary Examiner* — Thomas K Pham
*Assistant Examiner* — Jie Lei
(74) *Attorney, Agent, or Firm* — Albert L. Jacobs Jr.

(57) ABSTRACT

A machine and method for balancing across the brain's fusion bridge rivalrous stimuli of image pairs having diametrically opposed brightness and means of adjusting the rivalrous balance to measure the depth of a vision defect.

9 Claims, 23 Drawing Sheets

Right                                     Left

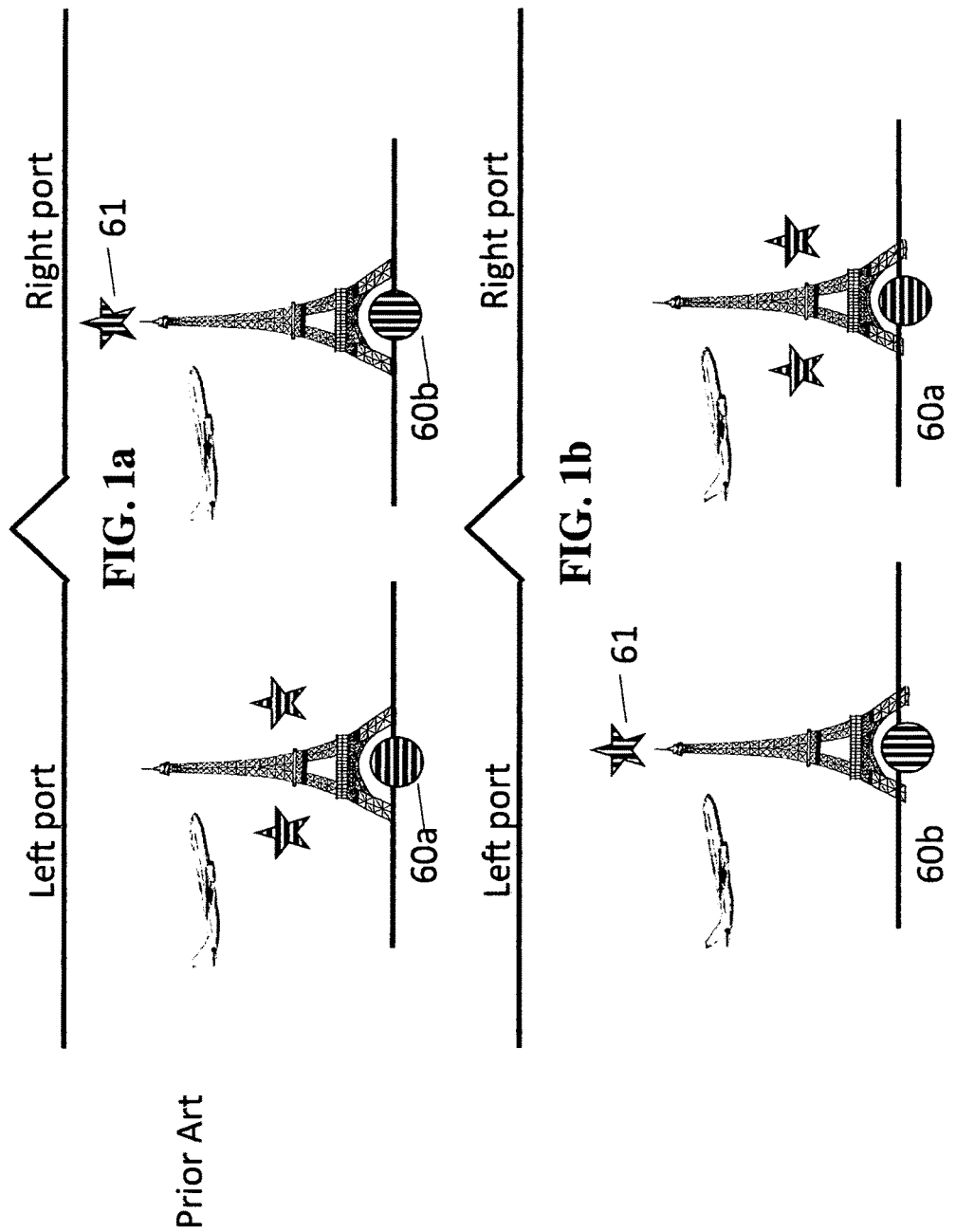

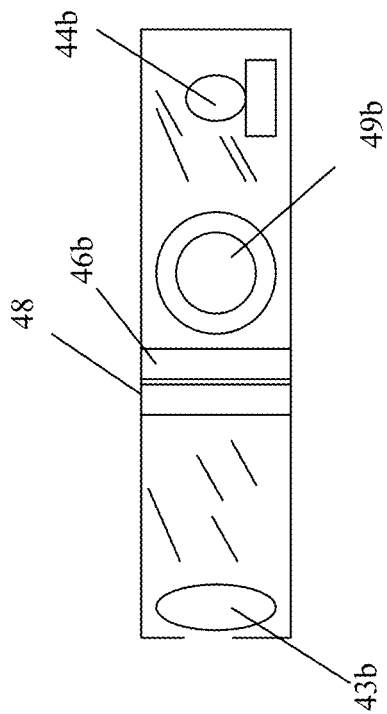
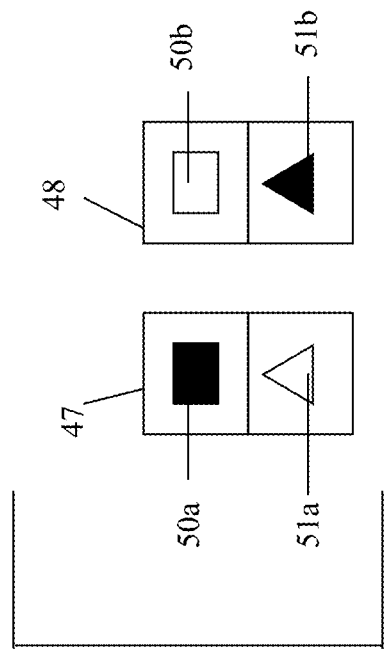
Fig. 6
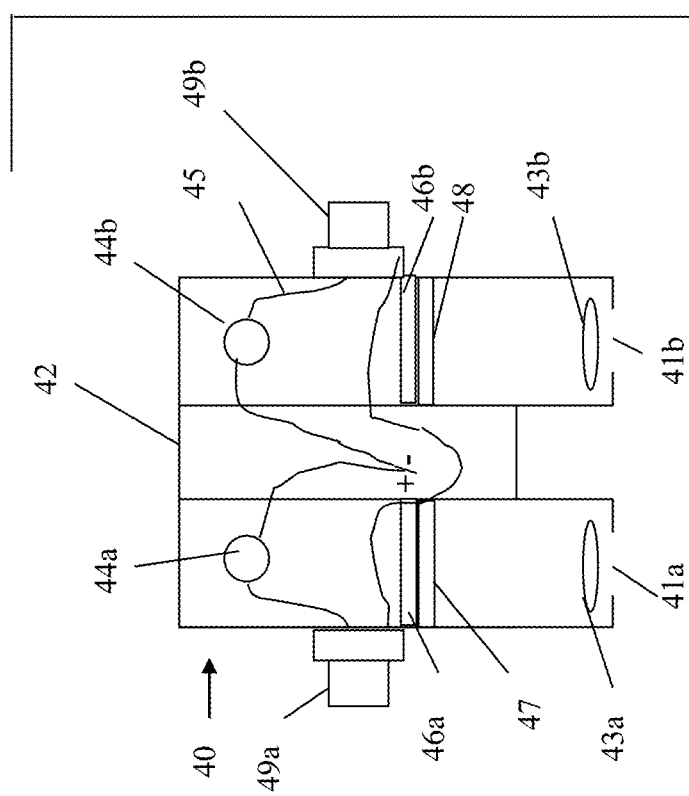
Fig. 7
Fig. 5

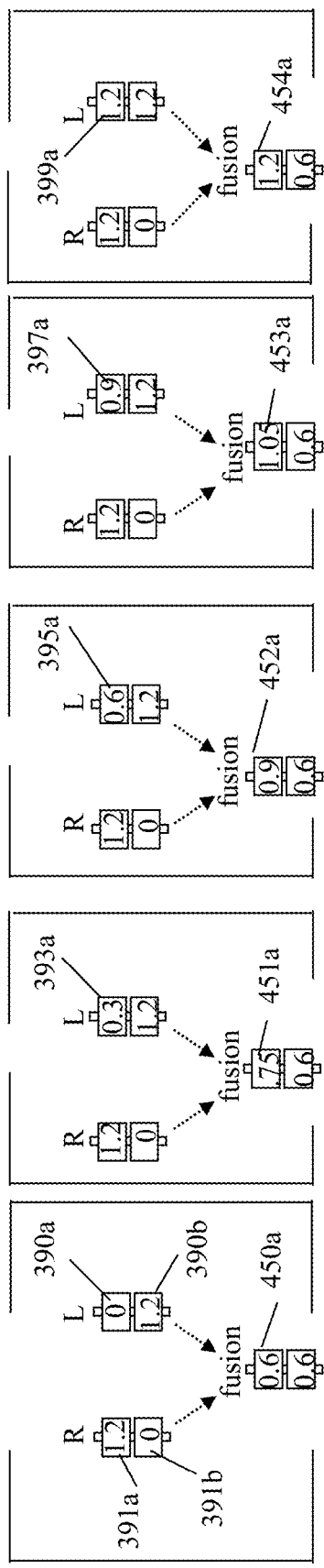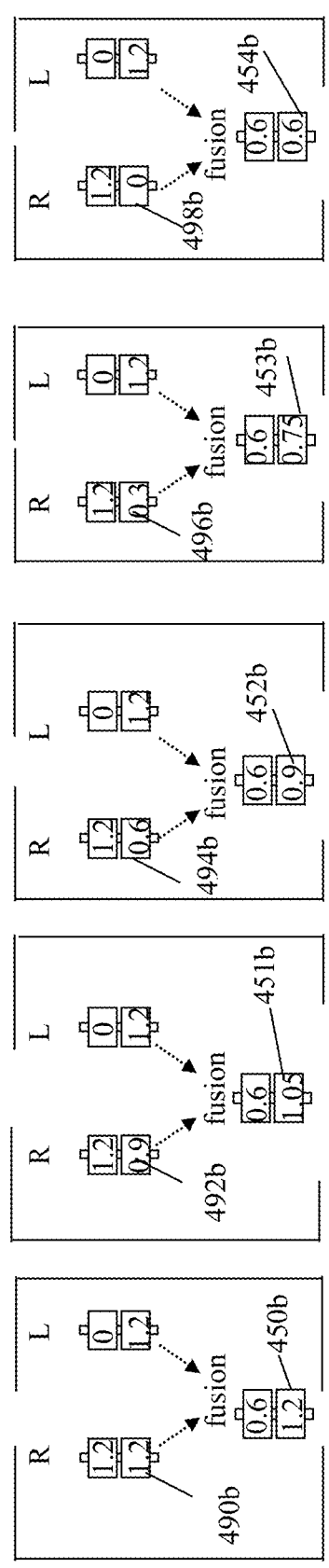
Numbers in squares = log density of stimulus or perception

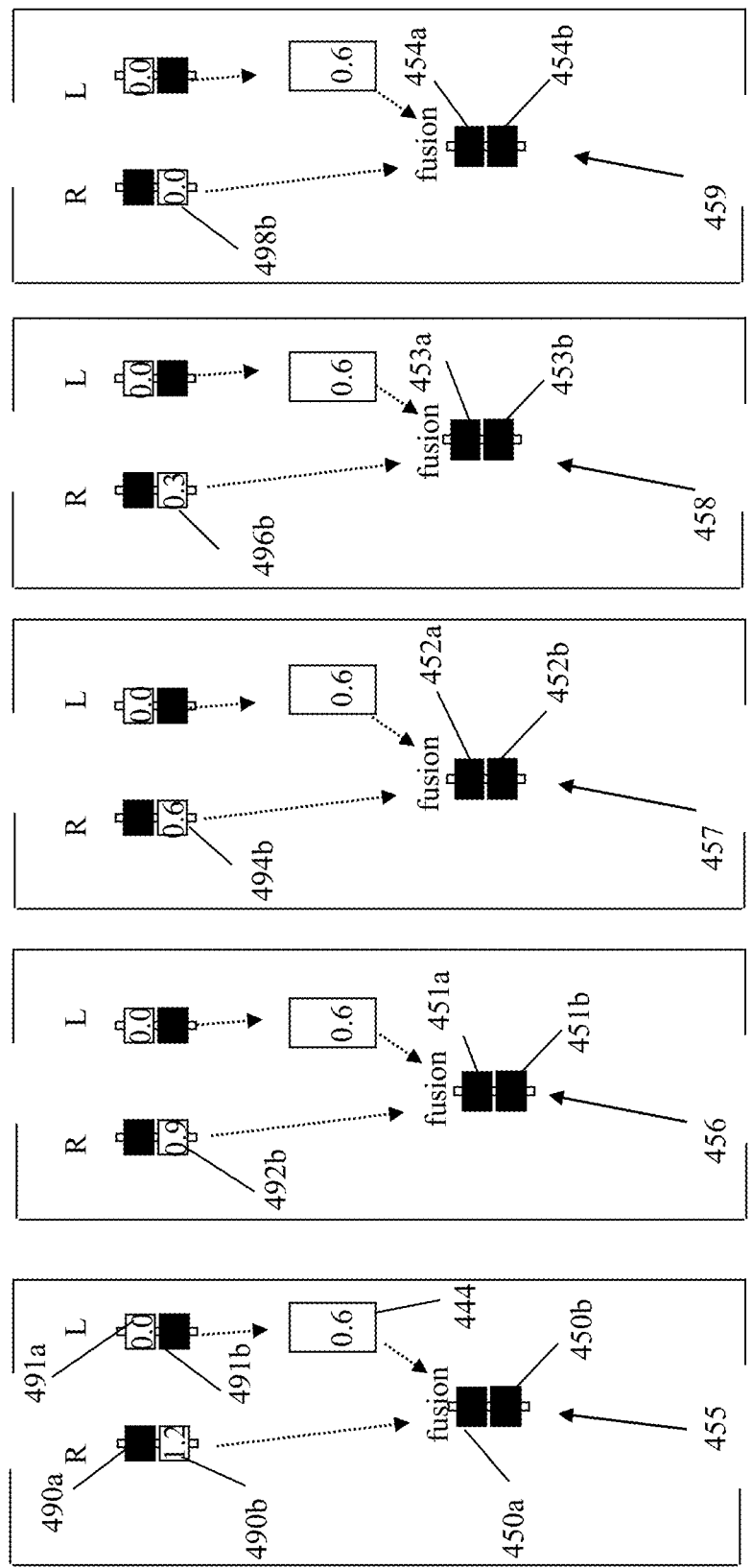

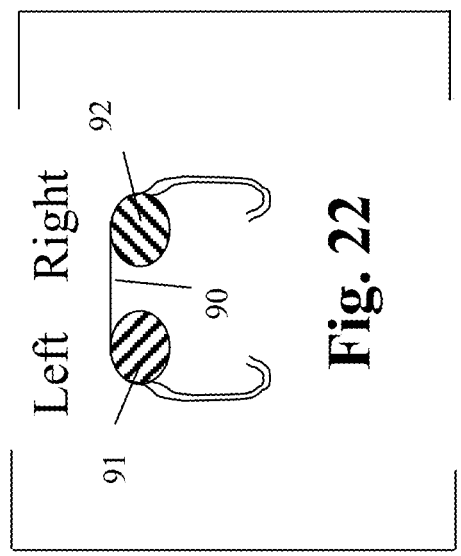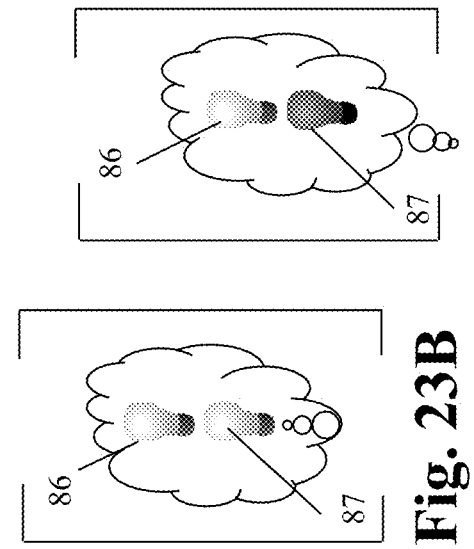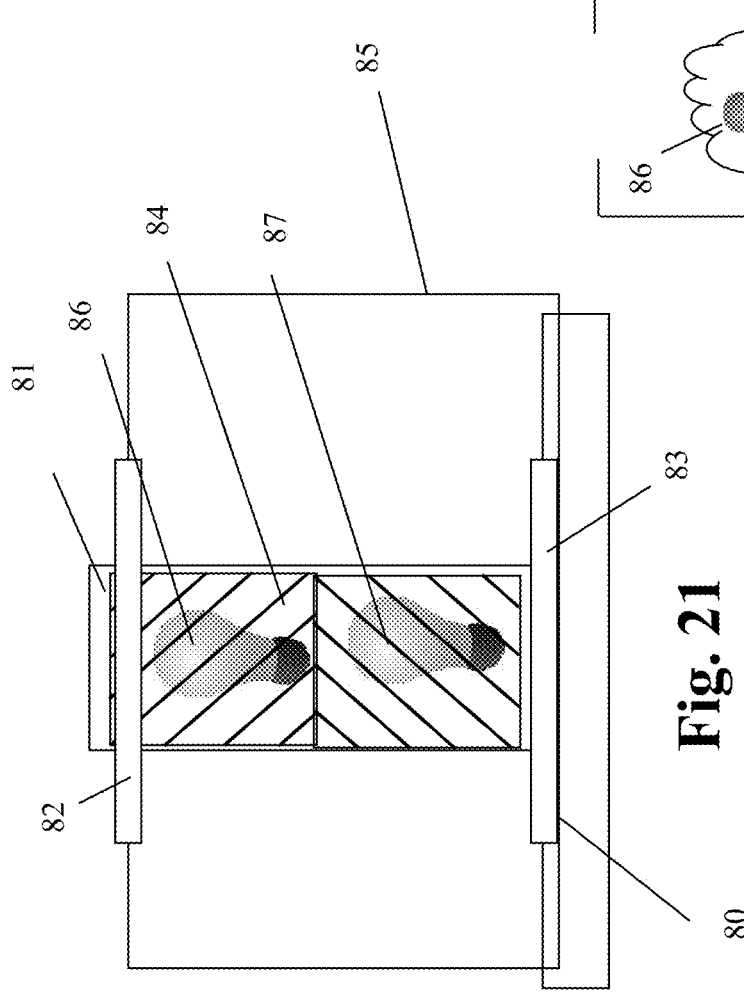

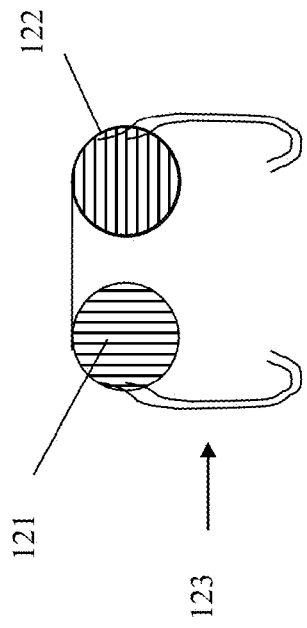
Fig. 25
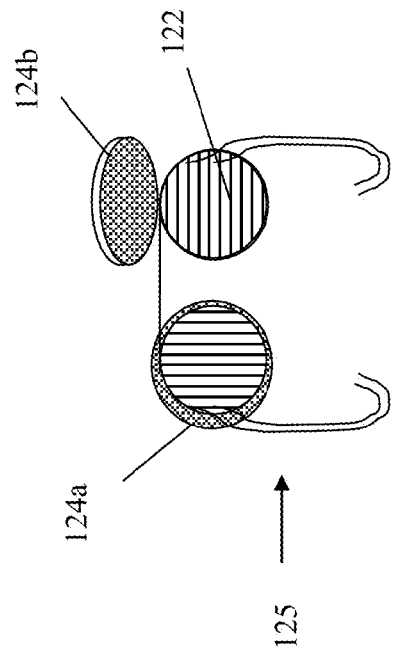
Fig. 26
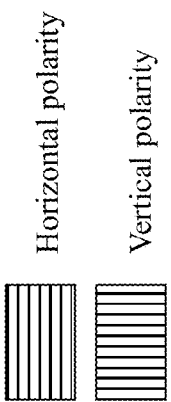
Horizontal polarity
Vertical polarity
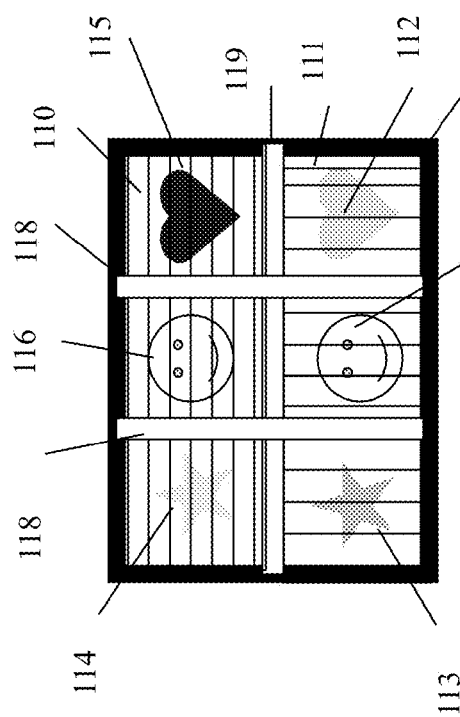
Fig. 24A
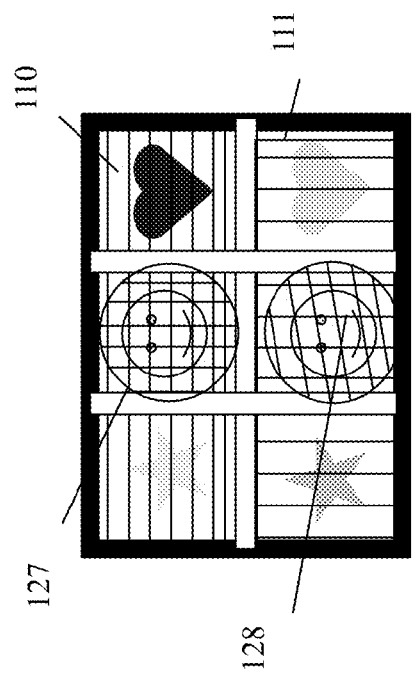
Fig. 24B

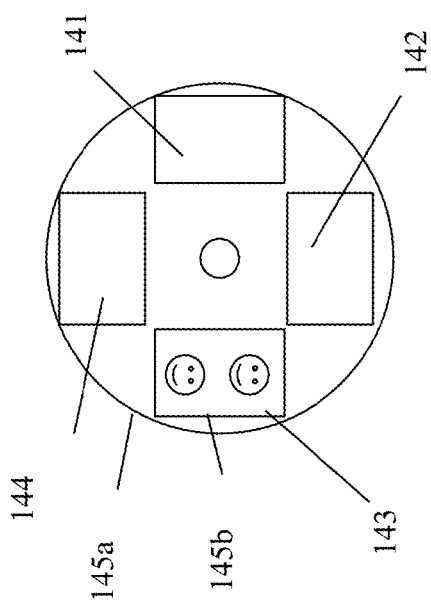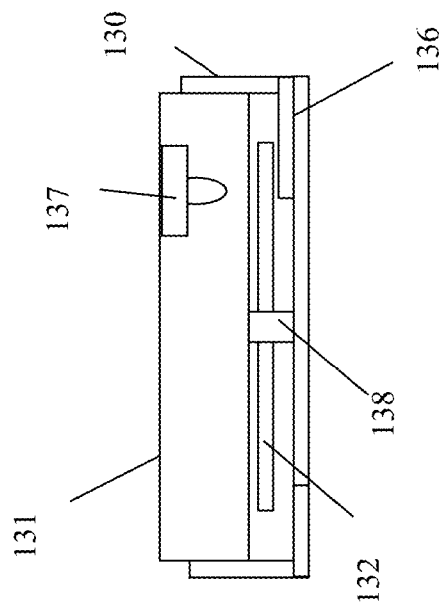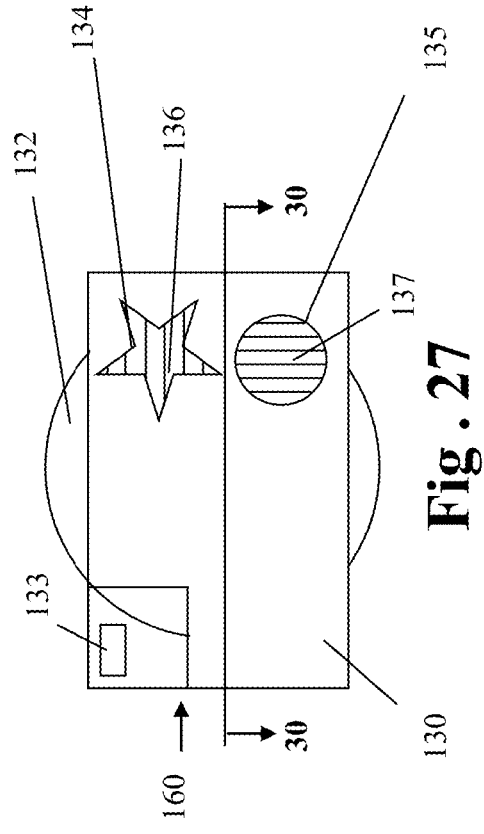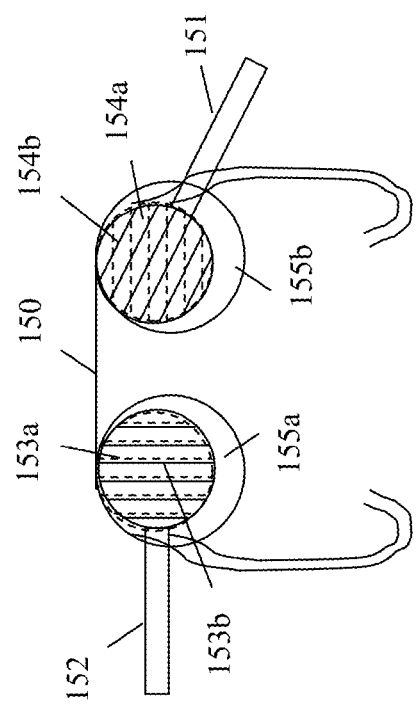

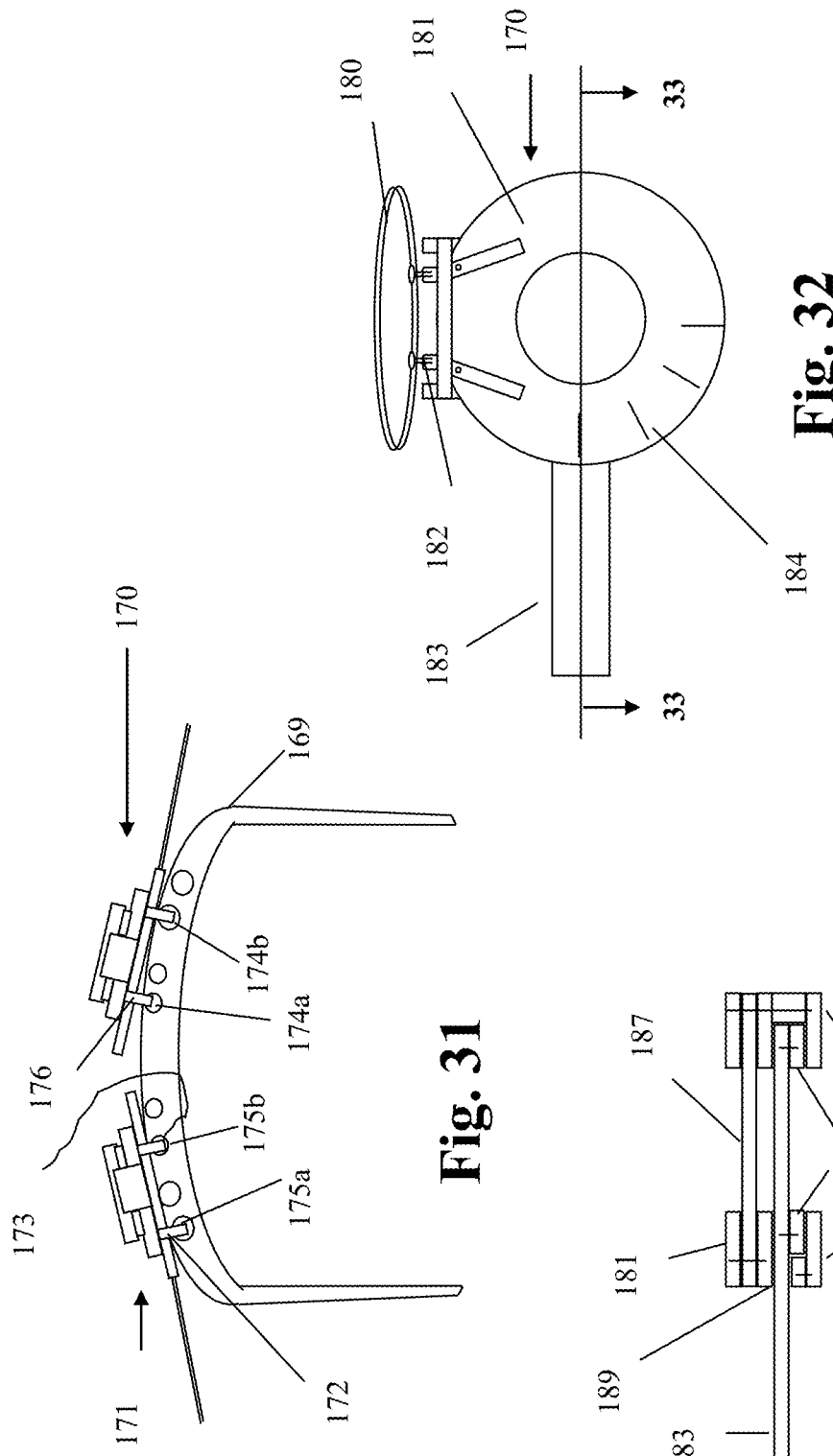

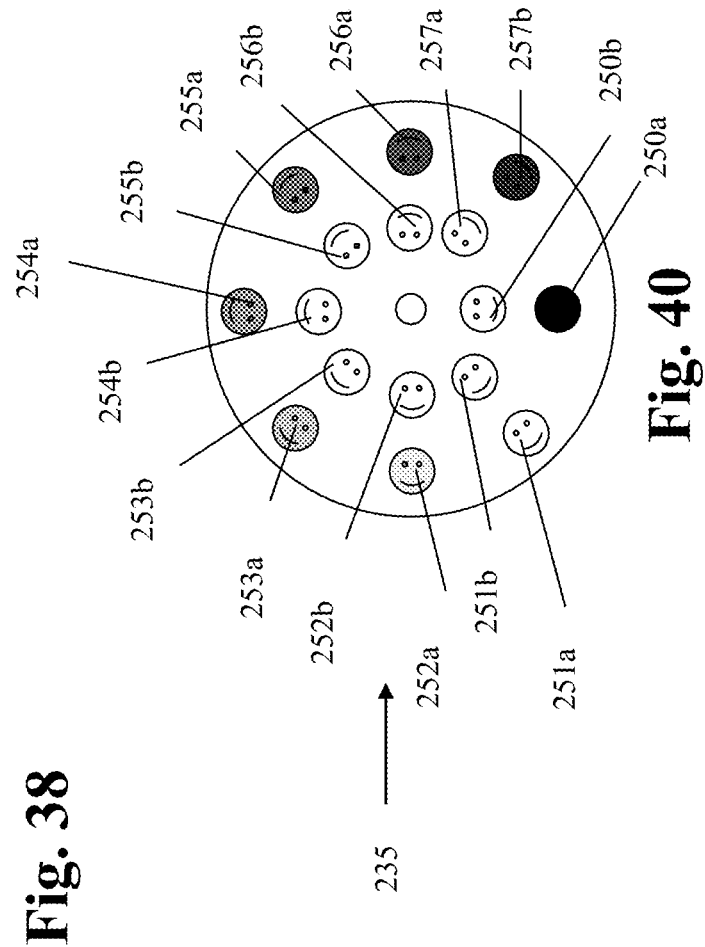

Fig. 47

AMBLYOMETER FOR BALANCING BRIDGING RIVALROUS BINOCULAR VISION

CROSS REFERENCE TO RELATED APPLICATIONS

Provisional patent application 61/627,815 dated Oct. 19, 2011

STATEMENT REGARDING FEDERALLY SPONSORED RESEARCH OR DEVELOPMENT

Not Applicable

DESCRIPTION OF ATTACHED APPENDIX

Not Applicable

INTRODUCTION

The visual system is divided into left and right subsystems and these subsystems are capable of functioning independently or cooperatively. In the case of stereopsis, the systems must work in concert to achieve depth perception. Vision rivalry, the competition between two dissimilar images is unnatural. When the eyes are not aligned, dissimilar images fall on corresponding retinal elements and double vision ensues. The images reaching perception are so dissimilar that the two cannot fuse into a single image and double vision occurs. The mind cannot deal with two grossly dissimilar images simultaneously, one image is disregarded and if not possible, one eye must be occluded from seeing the image.

It is possible to present dissimilar images to the two eyes by artificial means to create visual rivalry so that the integrity of the visual system can be measured. The dissimilarity of the images to induce rivalry may be in form (see U.S. Pat. No. 7,290,878) in color (see U.S. Pat. No. 5,764,340) or in brightness as will be described in the current invention. There is a limit to the degree of dissimilarity in form in order for fusion to occur; this is not true for brightness disparity. Paired images can be separately presented to the right and left vision subsystems by using a stereoscope, color filters, or polarizing filters. Using these tools, one can exploit the fusion process to discover the degree of interocular balance resulting from disease. Diseases intrinsic to the visual system can lead to a perceptual brightness disparity between the right and left subsystems. The brightness of the visual input to each eye can be manipulated to create a relative brightness disparity by attenuating the light to one eye or by presenting a less bright image to one eye. Controlling the monocular brightness input, a perceptual brightness disparity due to disease of the visual system can be brought into perceptual brightness equality to quantify the defect.

"Ambly" denotes dimness and my invention is called the Amblyometer, an instrument for (1) detecting perceptual difference in brightness between the two eyes and for (2) quantifying this difference by measuring the change in brightness necessary to bring the two sides of the visual system into balance.

My invention is to balancing the two sides of the visual system as the Wheatstone bridge is to balancing two sides of an electrical circuit.

As I describe my invention it will become evident that balancing four rivalrous images is a very sensitive measure of visual system imbalance. An analogy may be drawn between the electrical Wheatstone bridge and the psychophysical bridge of my invention, in that, both "bridges" have two parallel branches brought into balanced by adjusting one variable. My invention is the first vision test analogous to the Wheatstone bridge.

BRIEF SUMMARY OF THE INVENTION

My invention is the novel use of binocular stimuli to detect and measure brightness disparity between the right and left sides of the visual system that is distinct from prior art in that (1) form need not be part of the stimulus and (2) vertically aligned double (two pairs) rivalrous stimuli of reciprocal brightness are presented simultaneously that when fused create a perception of two vertically aligned images for comparison of relative brightness. Changing the brightness of one of the four stimuli can cause a misbalance of the system or can bring a misbalanced system into balance to quantify a defective visual system.

BRIEF DESCRIPTION OF THE DRAWINGS

The drawings constitute a part of the specifications and include exemplary embodiments to the invention, which may be embodied in various forms. It is to be understood that in some instances various aspects of the invention may be shown exaggerated or enlarged to facilitate an understanding of the invention.

FIGS. 1a, 1b and 1c. FIG. 1. Shows prior art of Hofeldt's U.S. Pat. No. 5,764,340 and a schematic of the Wheatstone bridge.

FIG. 7. Front view of image sets 47 and 48

FIG. 17B. Schematic of rivalrous set showing that 0.6 log defect in the left eye is over corrected by a 0.9 log attenuation over the right eye as indicated by darker bottom right dominant perception 451*b*

FIG. 17C. Schematic showing balanced rivalry by equally dark 152*a* right eye dominant perception and 152*b* left eye dominant perception FIG. 17D. Schematic of rivalrous set showing defect of 0.6 log defect in the left eye is under corrected where 0.3 log attenuation of the right eye indicated by darker top left perception 453*a*

FIG. 17E. Schematic of rivalrous set showing defect of 0.6 log defect in the left eye is under corrected where 0.0 log attenuation of the right eye indicated by darker top left perception 454*a*

FIG. 23B. Comparison of equally bright perception 87 and 86

FIG. 23C. Comparison relatively suppressed image 87 to brighter image 86

FIG. 24A. Frontal view of computerized picture viewer for presenting rivalrous images FIG. 24B. Frontal view of computerized picture viewer with cross polarizing filters FIG. 25. Rear view of spectacles holding polarizing filters FIG. 26. Rear view of spectacles holding polarizing filters and foldable neutral density filters FIG. 27. Frontal view of hand-held viewer with polarizing lenses over viewing ports FIG. 28. Disc for viewer 160 with different areas background colors and opacity FIG. 29. Rear view of spectacle holding cross polarizing filters for binocular separation and light attenuating FIG. 30. Cross sectional view of viewer 160

FIG. 31. Top view of clips 170 and 171 holding cross-polarizing filters and neutral density filters FIG. 32. Front view of clips 170 holding cross-polarizing filters and neutral density filters FIG. 33. Cross section view of clips 170 holding cross-polarizing filters and neutral density filters FIG. 34. Top view of hand-held viewer 240

FIG. 39. Top view of top 232 showing filters in the viewing window

FIG. 40. Frontal view of disc 235 showing stimuli of graded density

DETAILED DESCRIPTION OF INVENTION

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriate detailed invention, structure or manner.

Figure 1C:
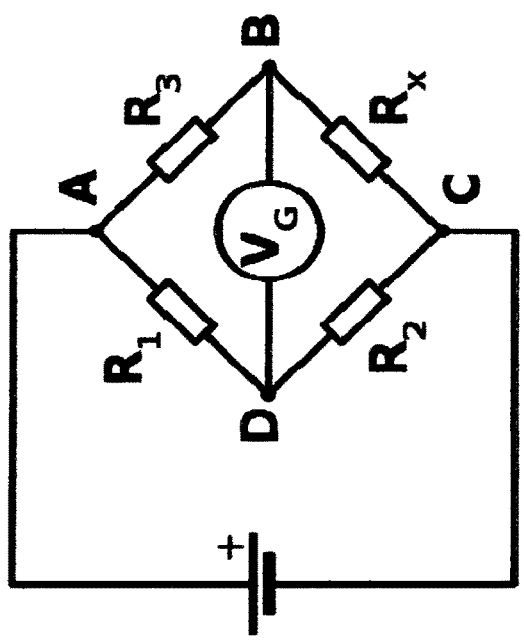

To better understand the present invention, Applicant refers to the prior art from Hofeldt (U.S. Pat. No. 5,764,340)

in FIGS. 1 a and 1 b consisting of slides presented in two View Master viewers for detecting and measuring a defect in either the right or left eye. Both View Masters are used in the testing protocol. The slide in FIG. 1 a is for detecting a defect in the right eye and the slide in FIG. 1 B is for detecting a defect in the left eye. To quantify a defect, a series of neutral density transparent filters mounting in two View Master discs is needed, one series arranged to measure a defect in the right eye and the other for measuring a defect in the left eye. In order to detect and quantify a defect in one eye by the method of Hofeldt, both viewers must be deployed and the endpoint is the point when red image 60b becomes dominant and matches the color of red non-rival reference image 61 (see FIGS. 1a and 1 b of current patent). Actually, at the point of fusion of red and blue colors, the perception is an alternating bluish-reddish color. The endpoint constitutes matching dominant red 60b image to a red color standard on two occasions and this raised the question are the two matches precise the same? When red color matching is the endpoint, the rivalry has passed the precise point where the red image and the blue image are equally perceived. At the red endpoint the eye viewing the red 60b image become dominant. This requires the examiner to record two endpoints and numerically compare the two endpoints. The current invention uniquely combines the two rival image pairs into a single perception for simultaneously comparison with the endpoint being the precise point of neutral rivalry and not when one eye becomes dominant. Besides providing an exact and reproducible endpoint without referring to a standard, the current invention eliminates three steps of Hofeldt's invention, (1) the need for two viewers, (2) recording of two endpoints, and (3) the endpoint reference, reference red star 61 is eliminated. The current invention presents the equivalent of Hofeldt's images 60a positioned above 60b in one eye and 60b positioned above 60a in the opposite eye and thus providing a novel vertically aligned reciprocal arrangement. For the current invention, the endpoint or the moment of equal sensory input for both eyes is when the fused top 60a and 60b appears identical to the fused bottom 60b and 60a images. Because color fusion may be confusing to the observer particularly for those with color vision defects, comparison of grey scale brightness (ideally 60a is white and 60b is black or vice versa) constitutes the preferred endpoint of the current invention. The stimuli are right-left side reciprocal, that is, the brightness of top image for one eye is the same brightness as the bottom image for the other eye. For quantifying a defect, the current invention needs not two but only one neutral density filter wheel having two series, one for dimming the right eye and one for dimming the left eye. To further understand my invention, I refer to the prior art in FIG. 1c consisting of a diagram of the Wheatstone bridge that shows parallel branches ABC and ADC, fixed resistors R1, R2, R3, variable resistor Rx, and galvanometer VG. The current invention provides a bridge across the right and left sides of the visual system and like the Wheatstone bridge has four elements to bring the system into balance. For the Wheatstone bridge changing the value of variable Rx balances the system and for my rivalrous bridge changing the brightness of one image balances the system as I shall describe later. The Wheatstone bridge is "bridged" by a galvanometer and my rivalrous bridge is "bridged" by rivalrous fusion. The Wheatstone bridge was invented by Christie in 1833 and was popularized by Charles Wheatstone in 1843. Wheatstone was the first to accurately describe binocular vision and he invented the stereoscope in 1852. There is no evidence that he proposed that the stereoscopic system could serve as a "Wheatstone bridge" to diagnose and measure visual dysfunction. KSR International Co. v. Teleflex Inc. (KSR), 550 U.S. 398, 82 USPQ2d 1385 (2007) is the standard for determining obviousness. The Examiner has failed to meet his burden under KSR to make a case for obviousness.

Figure 2B:
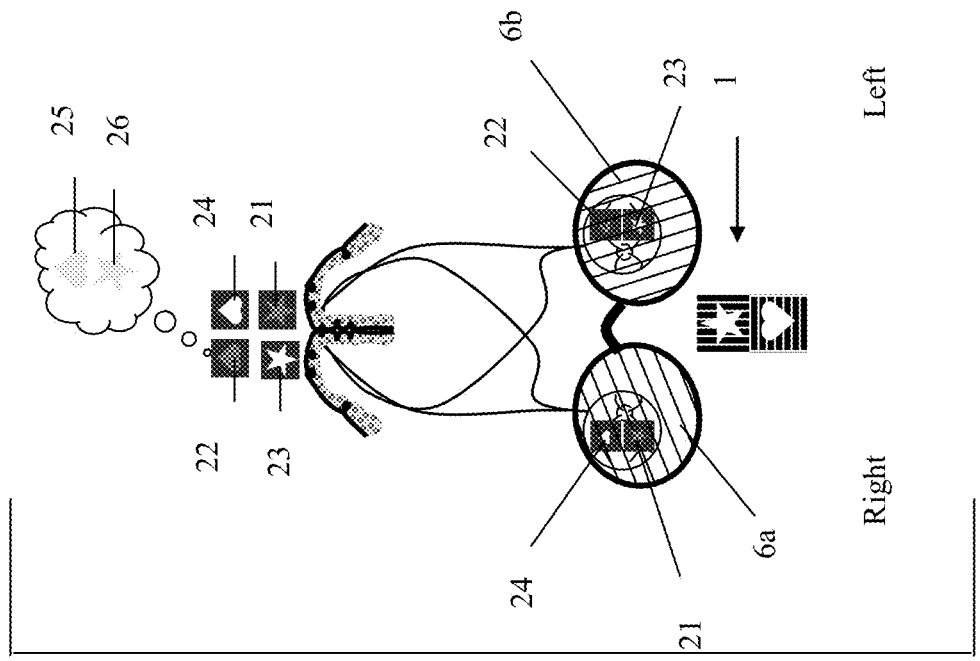
FIG. 2A. A schematic of the visual system pathways that process images using black and white rivalrous stimuli FIG. 2A. A schematic of the pathways that process images using light grey and white rivalrous stimuli FIG. 3. A schematic illustrating a vision defect is imposed to the left eye FIG. 4. A schematic illustrating balancing a left eye vision defect FIG. 5. Top view of hand-held stereoscope 40 with top removed FIG. 6. Side view drawing of stereoscope 40
Figure 2A:
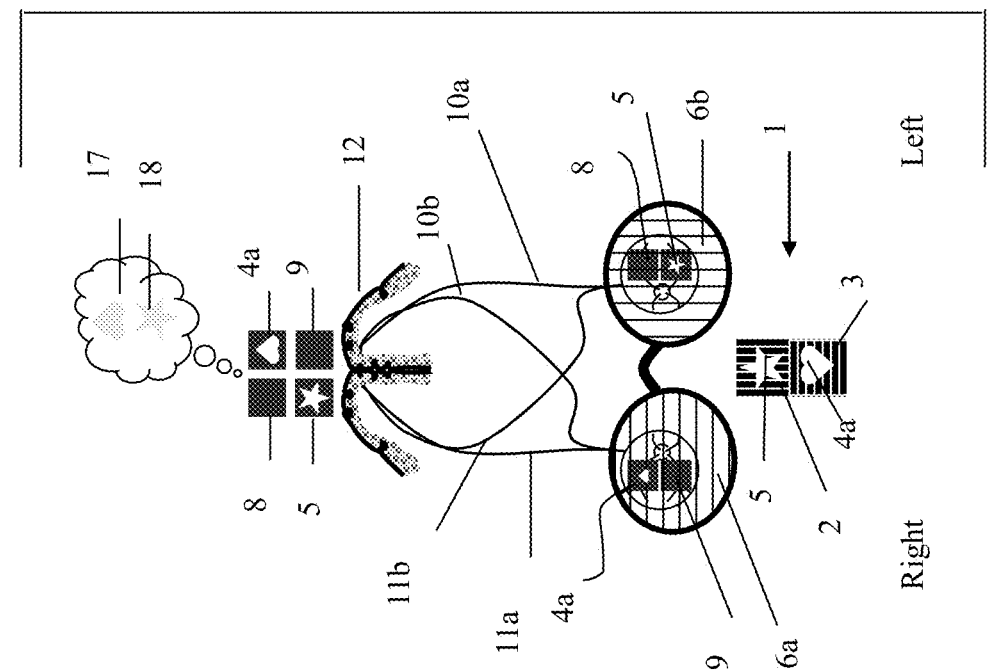

Illustrated in FIGS. 2A and 2B are the left and right sides of the visual system and the pathways that process images. In FIG. 2A image 1 consists of top white star 5 on a black background viewed through polarizing filter 2 oriented vertically and bottom white heart 4a on a black background viewed through polarizing filter 3 oriented horizontally. Heart 4a is transmitted vertically polarized through polarizing filters 3 and to reach the right eye while polarizing filter 6a blocks horizontally polarized star 5 from view of the right eye. Star 5 is transmitted through polarizing filter 6b to reach the left eye while heart 4a is blocked from view of the left eye by polarizing filter 6b. The left retinal image consists of top black background 8 and a bottom image star 5 and right retinal images consist of heart 4a and black background 9. Retinal images are transmitted to optic cortex 12 via pathways 10a, 10b, 11 a and 11 b where the perceived images are two rivalrous pairs, star 5 from the left eye paired with black background 9 from the right eye and heart 4a right eye paired black background 8 from the left eye. The two pairs fuse to form rivalrous right dominant perception 17 and left dominant perception 18. In the absence of visual system imbalance, perception 17 and 18 appear equally bright since they represent the average brightness of two diametrically opposed image pairs of the same brightness, that is, the brighter image of each pair is stimulating opposite eyes. When the right eye sees the brighter image, the right side dominates the rivalry and when the left eye sees the brighter image, the left side dominates rivalry. The background of one image pair needs not be formless or black to achieve rivalry as illustrated in FIG. 2B. By rotating polarizing filter 6b slightly away from the vertical alignment and rotating polarizing filter 6a the same amount from the horizontal alignment cross-polarization is reduced and light grey star 21 appears on background 9 and light grey heart 22 appears on background 8. At visual cortex 12, grey heart 22 and white heart 24 fuse to form right eye dominant perception 25 and white star 23 and grey star 21 fuse to form left eye dominant perceptions 26. Fused perceptions 25 and 26 appear equally bright since components, stars 21 and 23 and hearts 22 and 24, have the same average brightness.

Figure 4:
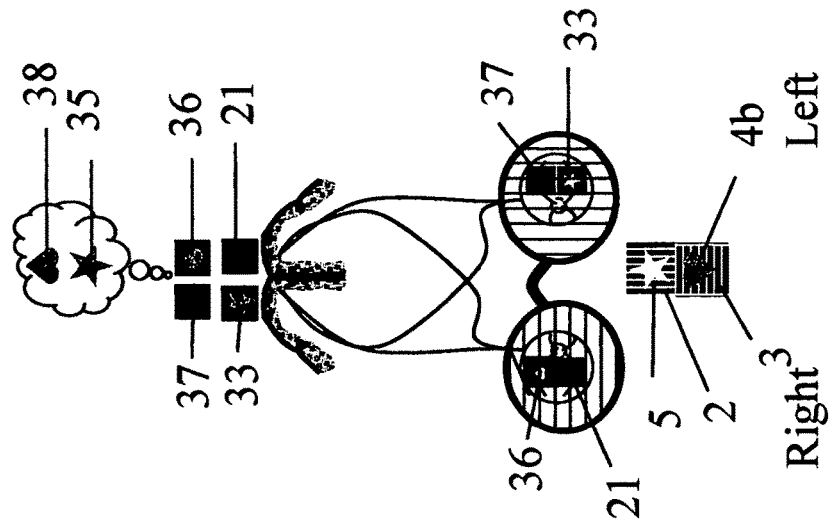
Figure 3:
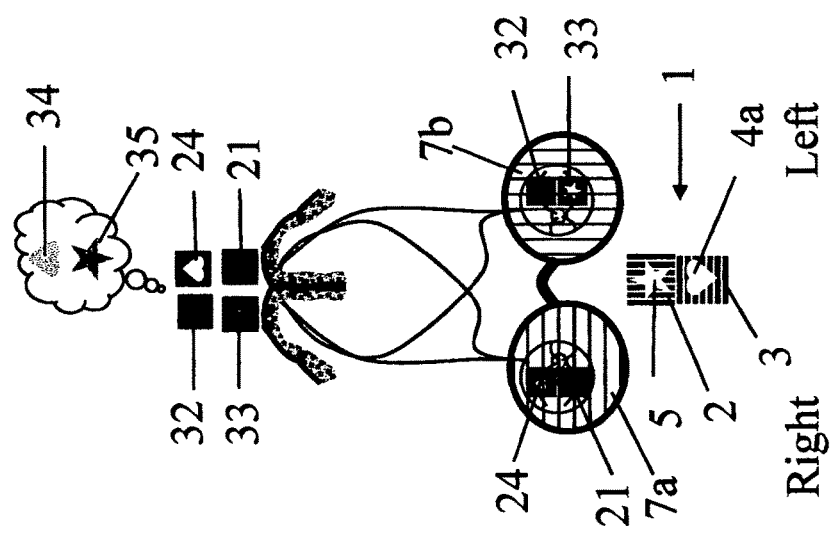

Let's now see how a defect in the left eye results in a perceptual imbalance and how my invention measures the defect by bring the two sides of the visual system into balance. In FIG. 3 a vision defect is imposed to the left eye. This left sided defect causes images viewed by the left eye to appear dimmer than images viewed by the right eye and is perceived at the level of the cortex as dim star 33 transmitted from the defective left eye as compared to bright heart 24 transmitted from the normal right eye. The average brightness of fused hearts 24 and background 32 is greater than the average brightness fused star 33 and background 21. As a result, perception of heart 34 appears brighter than star 35. Since star 35 is dim compared to heart 34, star 35 is relatively suppressed. This imbalance or relative difference becomes obvious to the observer under testing conditions because my invention positions the two images vertically aligned for direct brightness comparison. Bringing the system into balance quantifies the defect and this can be achieved in three ways, (1) by attenuating the light to the better eye with a neutral density filter (2) by reducing the brightness of the light source to the better eye or (3) by dimming the brightness of the image perceived by the better eye. As seen in FIG. 4, by reducing the brightness of heart 4a in FIG. 3 until the perception of the brightness of heart 38 and star 35 appears equal bright measures the size of left eye defect and this process requires dimming heart 4a seen by the right eye. Dimming heart 4a until perception of heart 38 and star 35 are equally bright is termed the neutralization endpoint.

My invention has several embodiments that utilize three different methods for separating binocular viewing, (1) a stereoscope in FIGS. 5 through 17, (2) complementary colored filters in FIGS. 18 through 20B, and (3) polarizing filters in FIGS. 21 through 47. In many of the drawings will appear an R for right and an L for left to clarify positioning. My first embodiment is illustrated in FIGS. 5 through 7. In FIG. 5 is illustrated stereoscope 40 which maybe hand-held or incorporated in an enclosure. In FIG. 5 hand-held stereoscope 40 is shown with the top removed to illustrate the interior elements. Stereoscope 40 with two separate viewing channels consists of housing 42; optical lenses 43a and 43b for placing images sets 47 and 48 into focus for a subject viewing though apertures 41a and 41b. Circuit 45 connects between a power supply of ac or dc current and rheostats 49a and 49b allow for individual brightness adjustment of bulbs 44a and 44b within the circuit. Diffuser 46a provides uniform illumination to image sets 47 and diffuser 46b provides uniform illumination to image set 48. In FIG. 6 is a side view drawing of stereoscope 40 in a see-through enclosure showing lens 43b, image set 48, diffuser 46b, and rheostat 49b and light bulb 44b. In FIG. 7 is image sets 47 and 48 consisting of paired rivalrous images 50a and 50b similar in shape and differing in brightness or contrast and rivalrous images 51a and 51b are similar in shape and differing in brightness or contrast. Images 50a and 51b are of similar brightness and contrast and images 51a and 50b are of similar brightness and contrast. Images 50a-51b may be of identical shape. While a subject is viewing illuminated images 47 and 48 through lenses 43a and 43b, the light intensity relative to the right and left sides is adjusted by rotating rheostat 49a or 49b to change the lighting intensity on one side relative to the other side until the perception resulting from the fusion of rivalrous images 50a and 50b and the perception resulting from the fused of rivalrous images 51a and 51b appear equally bright. The difference in the relative light intensity between the right and left sides when fused image pair 50a and 50b appears of equal brightness to fused image pair 51a and 51b is a measure of the degree of perceptual imbalance between the right and left sides of the visual system.

Figure 9A:
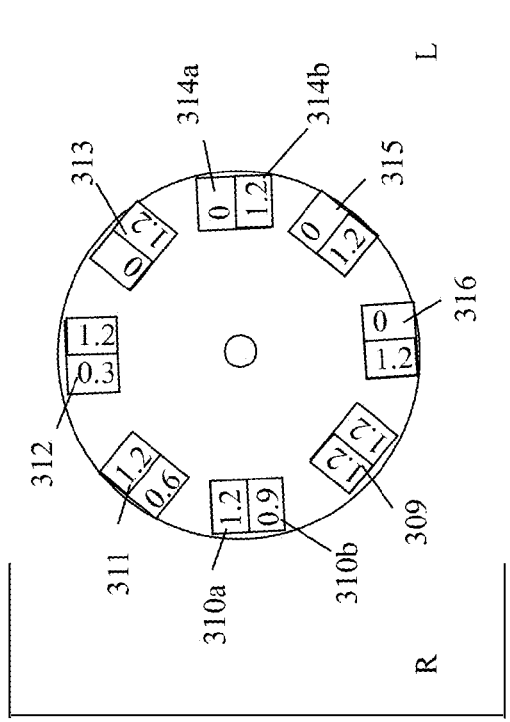
Figure 9B:
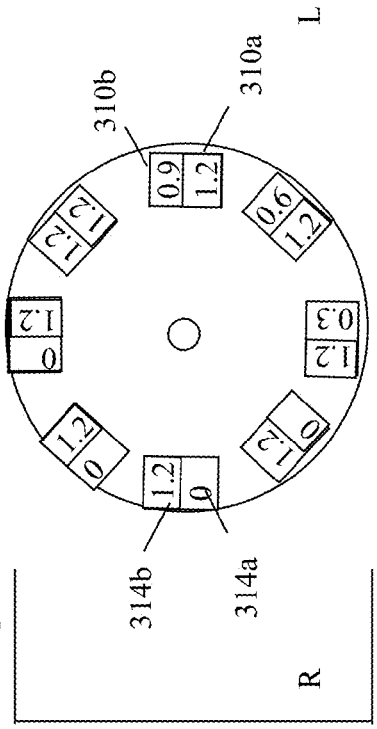
Figure 8A:
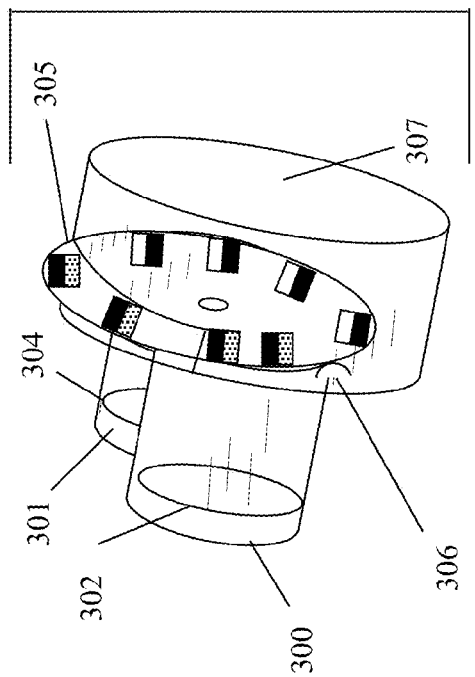
FIG. 8A. Perspective view of hand-held stereoscope with reel 305
Figure 10A:
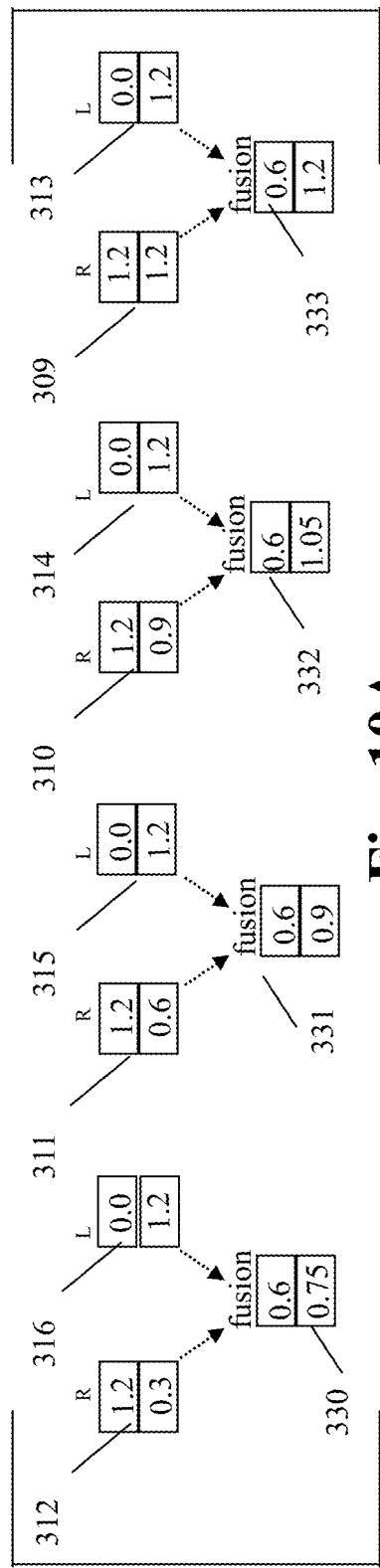
FIG. 10A. Schematic of a series of stimuli to progressively attenuate the right eye to measure a left eye defect FIG. 10B. Schematic of a series of stimuli to neutralizes a right eye FIG. 11. Schematic showing two computers feeding two miniature monitors mounted on spectacle frames for separating binocular images and testing rivalry FIG. 12A. Frontal view of monitor showing attached divider 360 to set testing distance and separate binocular vision FIG. 12B. Side view of monitor and divider 360 with curtained ferruled FIG. 13A. Frontal view of monitor showing attached divider 360 with unferruled curtain separating binocular vision FIG. 13B. Side view of monitor showing attached divider 360 with unferruled curtain FIG. 14A. Frontal view of divider 360 with base-out prism attached FIG. 14B. Side view of divider 360 with base-out prism attached FIG. 14C. Top view of spectacles attached with base-out prisms and neutral density filters FIG. 14D. Top view of spectacles, base-out prisms and neutral density filters 379 raised FIG. 15A. Schematic of rivalrous set showing brightness balance with top 0.6 log right eye perception and bottom 0.6 log left eye perception FIG. 15B. Schematic of rivalrous set showing brightness imbalance with top 0.75 log right eye perception and bottom 0.6 log left eye perception FIG. 15C. Schematic of rivalrous set showing brightness imbalance with top 0.9 right eye perception and bottom 0.6 log left eye perception FIG. 15D. Schematic of rivalrous set showing brightness imbalance with top 1.05 log right eye perception and bottom 0.6 log left eye perception FIG. 15E. Schematic of rivalrous set showing brightness imbalance with top 1.2 log right eye perception and bottom 0.6 log left eye perception FIG. 16A. Schematic of rivalrous set showing brightness imbalance with top 0.6 log right eye dominant perception and bottom 1.2 log left eye dominant perception FIG. 16B. Schematic of rivalrous set showing brightness imbalance with top 0.6 log right eye dominant perception and bottom 1.05 log left eye dominant perception FIG. 16C. Schematic of rivalrous set showing brightness imbalance with top 0.6 log right eye dominant perception and bottom 0.9 log left eye dominant perception FIG. 16D. Schematic of rivalrous set showing brightness imbalance with top 0.6 log right eye dominant perception and bottom 0.75 log left eye dominant perception FIG. 16E. Schematic of rivalrous set showing brightness balance with top 0.6 log right eye dominant perception and bottom 0.6 log left eye dominant perception FIG. 17A. Schematic of rivalrous set showing that 0.6 log defect in the left eye is over corrected by a 1.2 log attenuation of the right eye as indicated by darker bottom right dominant perception 450*b*
Figure 10B:
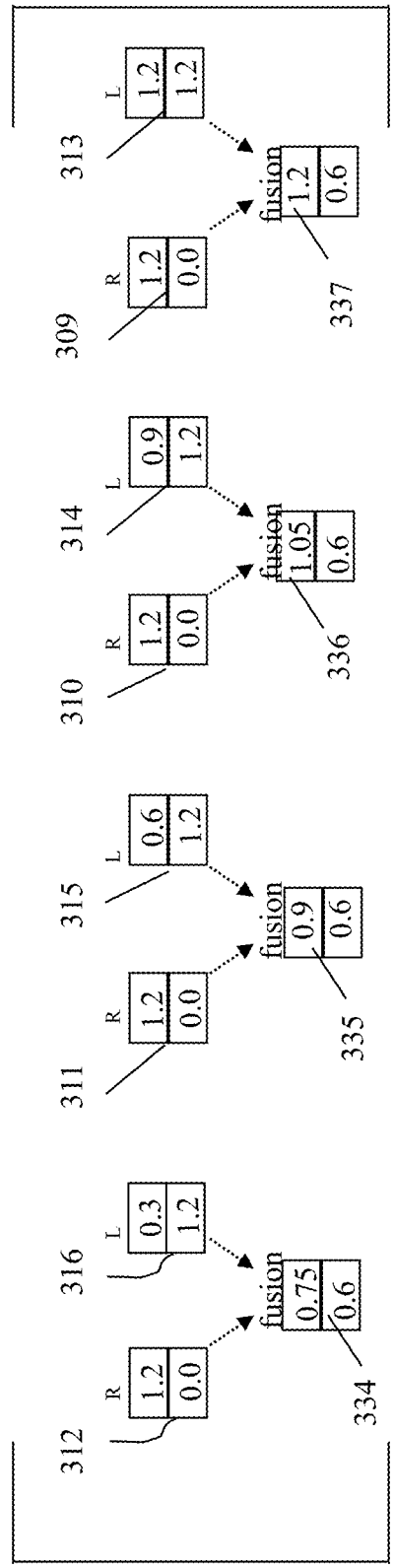

In FIG. 8A is another stereoscope having eyepieces 300 and 301, focusing lenses 302 and 304, reel 305, reel stops 306 and light port 307. In this embodiment the optical density of the different images attenuates light to one eye or the other. In disc 305 the optical densities range from 0 log units to 1.2 log units but discs may be of other incremental progression and may extend to 3 or more log units. The disc is removable and multiple discs may be used to extend the optical density testing range. One optical density arrangement is seen in FIG. 9A in which each eye views a vertically aligned top and bottom image with the top right and left images serving as a rivalrous pair and the bottom right and left images serving as a second rivalrous pair. In this arrangement there are two progressive light attenuation series of four right and left rivalrous sets with each set made up of 4 images with only one image, the variable image, sequentially changing in density in the series. For example one set is made up of images 310a and 310b viewing by the right eye and images 314a and 314b viewing by the left eye. Images 310a and 314a are a rivalrous pair and 310b and 314b are a rivalrous pair and as a group the 4 images constitute one set for measuring a 0.9 log defect in the left eye since the variable density image is 310b dimming the right eye (dims the better eye). In FIG. 10A is illustrated a series that progressively attenuates the right eye to measure a defect in the left eye, set 312 and 316 neutralize a 0.3 log defect, set 311 and 315 neutralize a 0.6 log defect, and set 309 and 313 neutralizes a 1.2 log defect. Rotating disc 305 by 180 degrees inverts the densities and provides the same progressive series to neutralizes a defect in the right eye since the variable image of each set dims the left eye as illustrated in FIG. 10B.

Figure 8B:
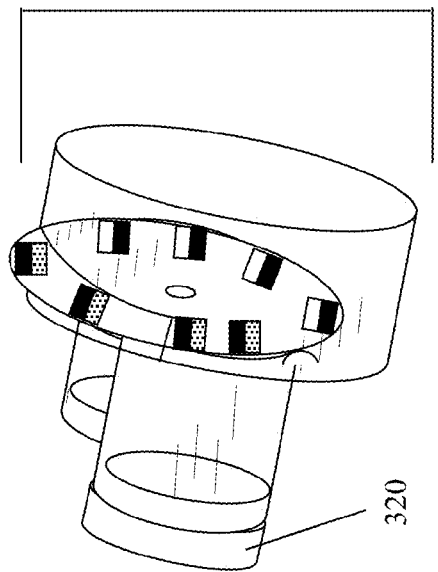
FIG. 8B. Perspective view of hand-held stereoscope with neutral density filter 320 attached to right viewing eyepiece FIG. 9A. Frontal view of reel 305 showing progression optical density of stimuli FIG. 9B. Frontal view of reel 305 rotated 180 degrees from FIG. 9A.

To confirm and to amplify a dimness defect, my stress test is used. In FIG. 8B is neutral density filter 320 that fits over the right or left eyepiece to induce intraocular brightness disparity. Filter 320 may be of any optical density, but for this example it is a 0.9 log density filter. Placing filter 320 over the left eyepiece, neutralization occurs when the variable density image 310b is rotated for viewing through the right eye and counter-balances the 0.9 log density of filter 320 attenuating the left eye. Next 0.9 log filter 320 is placed over the right eyepiece and neutralization occurs when variable density filter 310a is rotated for viewing through the left eye to counter-balance filter 320 dimming the right eye. In the absence of defective vision, the variable filter density to neutralize the intraocular disparity is the same density for both sides. On the other hand, if defective vision of 0.3 log units is present in the left eye, 0.9 log filter 320 over the right eyepiece imposed an interocular disparity of net 0.6 log units (0.9 log filter 320 right eyepiece minus 0.3 log left eye defect) and is neutralized by rotating 311 variable image of 0.6 log density over the left eye. Then by placing filter 320 of 0.9 log over the left eyepiece imposes a net interocular difference of 1.2 log units (0.3 left eye defect plus 0.9 filter 320 left eyepiece) and is neutralized by rotating variable image 309 density of 1.2 log units over the right eye. The neutralization endpoint with filter 320 over the defective left eye is 1.2 log units and with filter 320 over the healthy right eye is 0.6 log units, a difference of 0.6 log units, twice the size of the 0.3 log vision defect in the left eye. The stress test doubles the size of the defect. The stress test in a useful method to identify and measure small defects and confirms reliability by repeating rivalrous neutralization.

Figure 11:
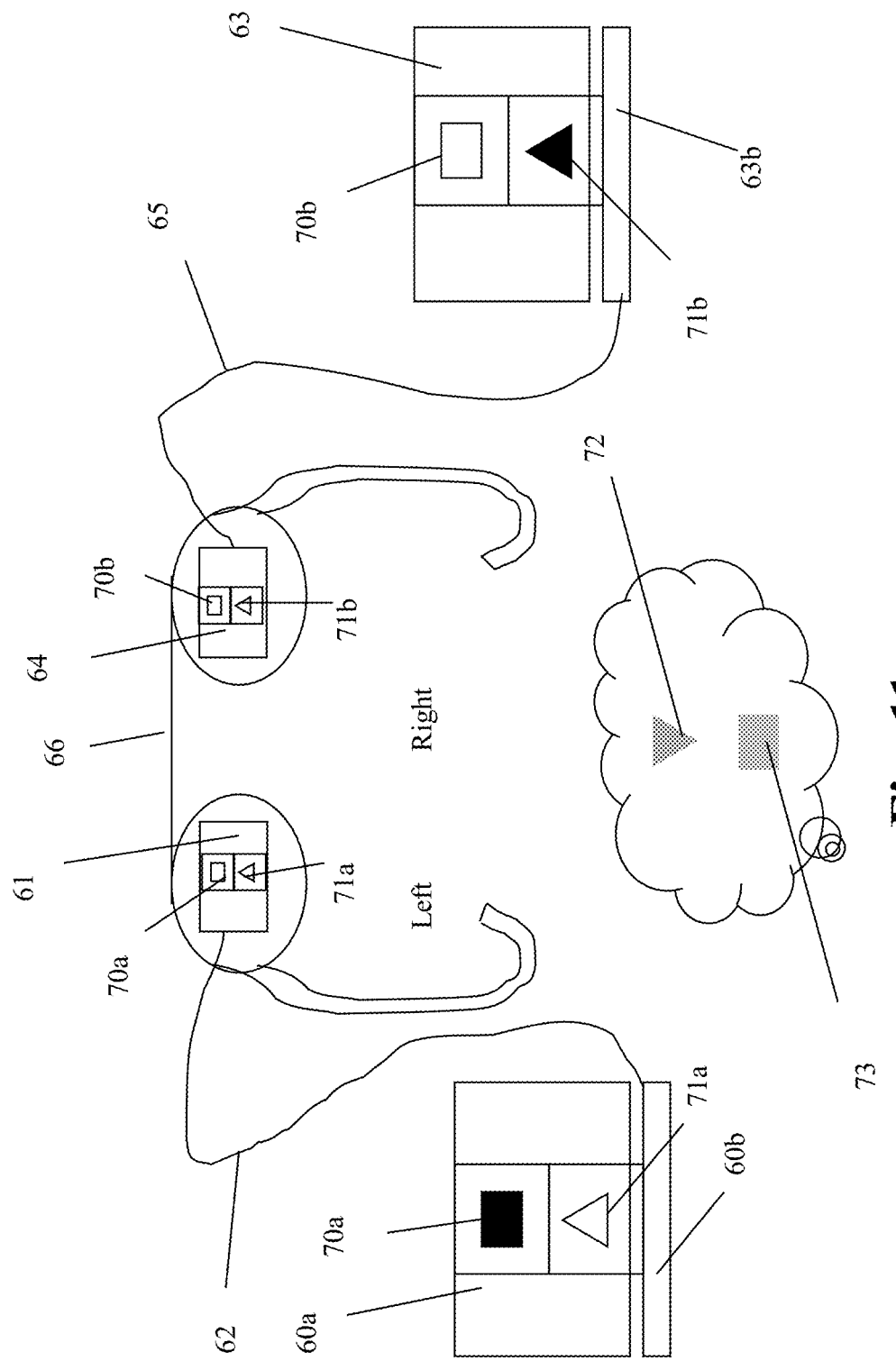

Another embodiment is seen in FIG. 11 where binocular separation by way of two computers feeding two miniature monitors mounted on spectacle frames so that computer generated images seen by the right and left eyes can differ as to shape, color, contrast, and brightness. Alternatively, one computer having a separate channel to each of the two spectacle displays may also be used as long as the images to each spectacle display can be independently controlled. Computer monitor 60a is connected to computer 60b, which connects to spectacle display 61 mounted on the left side of frames 66 through cable 62. Computer monitor 63a is connected to computer 63b, which connects to spectacle monitor 64 mounted on the right side of frame 66 through cable 65. Computers 60b and 63b may also be connected to spectacle monitors 61 and 64, respectively by a wireless network. With this embodiment a limitless number of rivalrous image pairs, such as, image pair 70a and 70b and image pair 71a and 71 b can be presented to a subject wearing spectacles 66. The simplest method of testing is to maintain 3 of the 4 images constant and to vary the brightness of one image, the variable image, until the rivalrous image pairs aligned vertically appear equally bright. With a right eye defect, triangle 72 appears brighter than square 73. With a left eye defect, square 73 appears brighter than triangle 72. To measure a right eye defect, triangle 71*a*, the variable image is dimmed and to measure a left eye defect, square 70*b*, the variable image, is dimmed. The amount of brightness attenuation of an image to achieve the perception of brightness equality of square 73 and triangle 72 is a measure of the size of the vision defect.

Figure 13:
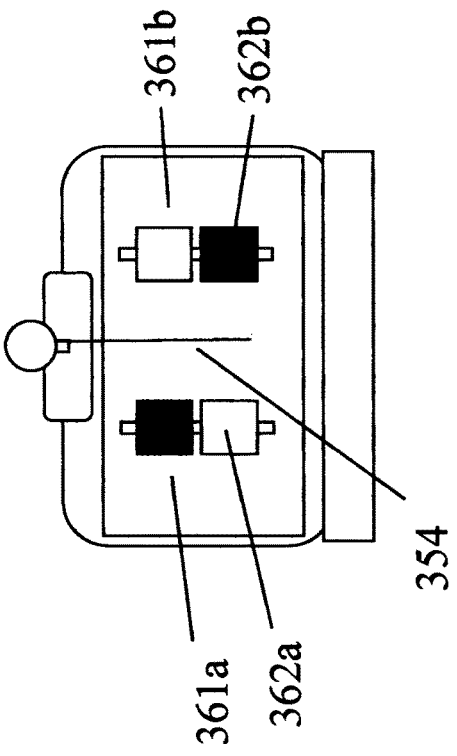
Figure 13B:
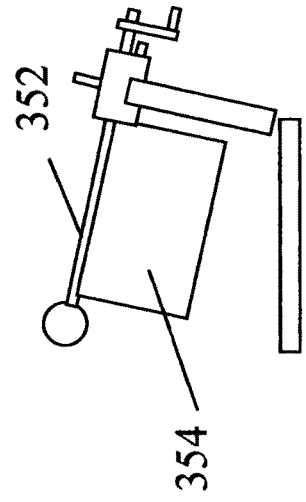
Figure 12A:
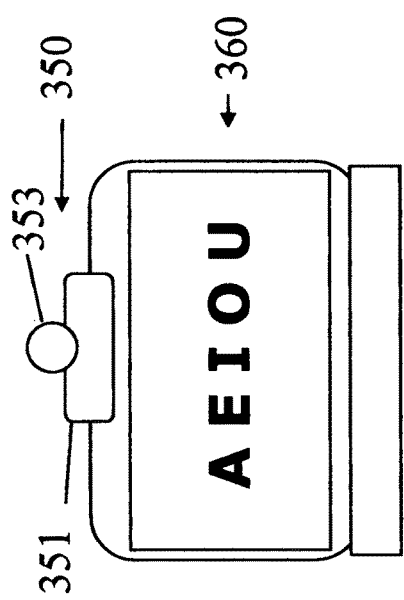
Figure 12:
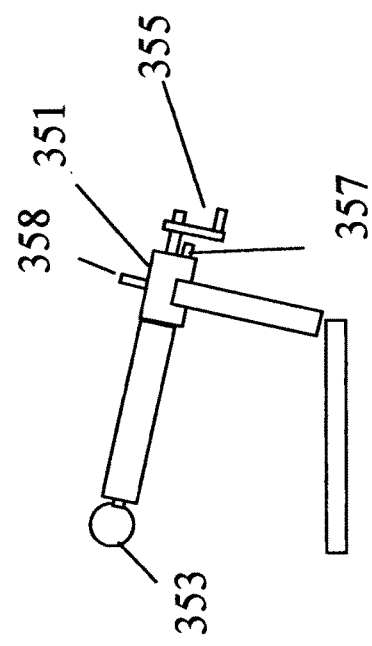
Figure 14A:
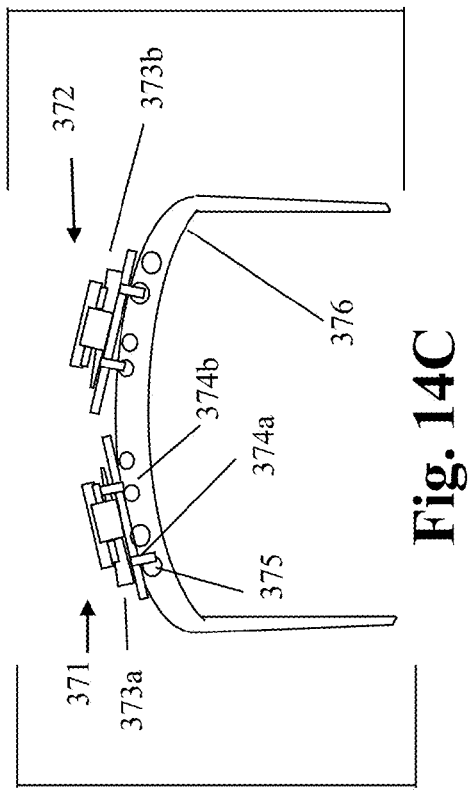
Figure 14C:
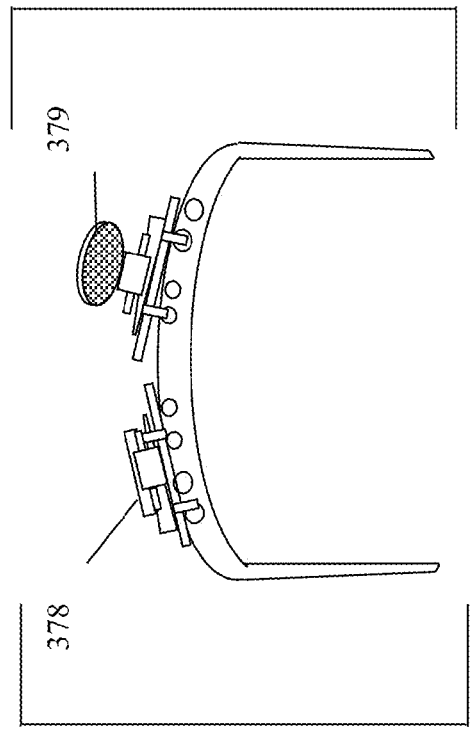
Figure 14B:
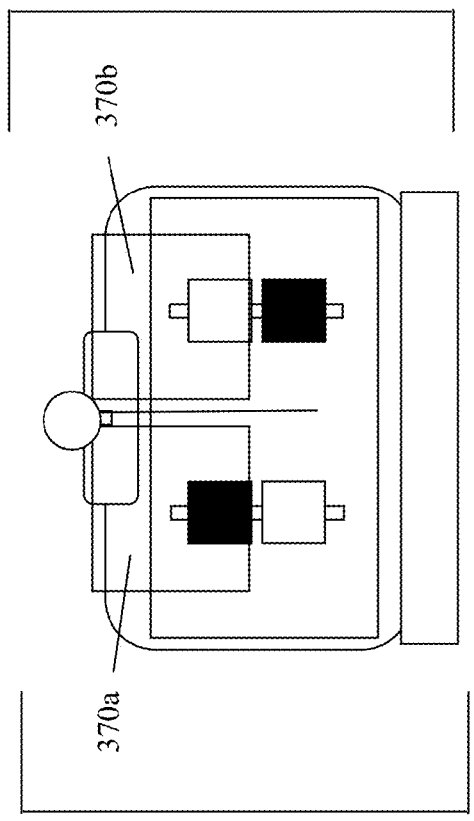
Figure 14D:
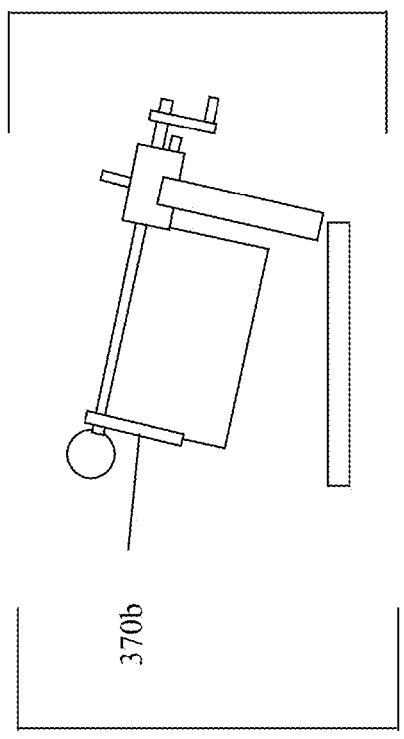

Another embodiment of my invention using computer-generated images is seen in FIGS. 12A through 17E where binocular separation of rivalrous images is provided by presenting right and left rivalrous images on a computer screen and using a screen divider to block the view of monocular images from the opposite eye. Divider 350 mounts onto a computer monitor as shown in FIG. 12A. The divider constructed of plastic or other material and is composed of base 351 that attaches to the monitor of computer 360 and secured by setscrew 357. Shaft 352 with ball 353 or other cushioning material attached fits against the forehead of the subject and passes through base 351 which is secured to computer 360. The length of shaft 352 determines the testing distance between the subject and the computer monitor. Mounted to shaft 352 is curtain 354 blocking from view the images seen by the contra-lateral eye. Curtain 354 may be raised or lowered by crank 355 and the rotation of shaft 352 is locked by setscrew 358 to maintain a desired length of curtain 354. When curtain 354 is ferruled it serves as a testing distance measuring standoff for any vision test utilizing a monitor, for example a visual acuity test as depicted by letters 350 in FIGS. 12A and 12B. With curtain 354 unferruled, divider 350 serves to separate binocular image pairs, such as images 361*a* from 361*b* and 362*a* from 362*b* as seen in FIGS. 13A and 13B. Many subjects can fuse images correctly positioned horizontal stereo image pairs as shown in FIG. 13A by pairs 361*a* and 361*b* and pair 362*a* and 362*b* without the aid of base-out prisms. However some subjects require base-out prism for fusion, as shown in FIG. 14A, left base-out prism 370*a* and right base-out prism 370*b* are provided in order to fuse stereo image pairs. Alternatively, prisms 373*a* and 373*b* can be attached to the frame of spectacles 376 as seen in FIGS. 14C and 14D and the spectacle are worn during testing. Prism 373*a* is mounted to clip 371 having clasp 374*a* and clasp 374*b* fitting through hole 375 on the left side of spectacles 376. The holes chosen to mount the to frame 376 is dictated by the interpupillary distance of the subject. Clip 372 with prism 373*b* and neutral density lens 379 attaches to the right side of spectacles 376. Neutral density lenses 378 and 379 may be raised and lowered for change the brightness of images viewed by the subject. In FIGS. 15A-15E are shown left (L) and right eye (R) stimuli and the perceptions of the two stimuli by a normal subject. In FIG. 15A top stimulus 390*a* and bottom stimulus 390*b* viewed by the left eye are rivalrous with top 391*a* and bottom 391*b* viewed by the right eye. Since 390*a* and 391 *b* have 1.2-log attenuation and 390*b* and 391*a* have zero attenuation, the fusion of this set gives perceptions 393*a* and 393*b* of equal brightness. Using a series of decreasing image brightness of the variable image as illustrated in FIGS. 15A-15E or increasing image brightening (reducing attenuation) of the variable image as illustrated in FIGS. 16A-16E to dim the vision in the better eye is a method of quantifying a vision defect. The brightness of the top variable stimulus for the left eye is progressively attenuated by 0.3 log units increments as seen by increasing filter density from 0 in 390*a* to 1.2 log units in 399*a* which causes the top perception to progressive dim from mean density of 0.6 log in 450*a* perception to 1.2 log unit in perception 454*a*.

In FIGS. 16A-16E the brightness of the variable bottom stimulus to the right eye is progressive brightened by 0.3 log units from to 498*b*, which causes the fused perception to progressive brighten as illustrated by perception 450*b* of 1.2 log density brightening to 0 log attenuation perception 454*b*. In the presence of a visual defect, neutralization occurs when fused perceptions appear of equal brightness and this is achieved by dimming the variable image seen by the normal eye to match the brightness of the perception seen by the opposite eye with the defect. In FIGS. 17A-17E is illustrated the method of neutralizing a 0.6 log unit defect 444 in the left eye of a subject when the darkest stimuli 490*a* and 491 *b* attenuates light 100%. When the darkest stimuli are 100% attenuated, the light attenuation of a vision defect cannot further change the light attenuation, making the values of these stimuli constant and analogous to the fixed resistors in the Wheatstone bridge. In FIG. 17A left eye dominant perception 450*a* image appears brighter than bottom right eye dominant 450*b* perception. This is because variable stimuli 490*b* of 1.2 log density attenuates light more in the right eye than does 0.6 log defect in the left eye. In FIG. 17C, perceptions 452*a* and 452*b* appear equally bright and are the neutralization endpoint because the light attenuation on the left and right sides are equal, that is, 0.6 log attenuation of image 494*b* viewed by the right eye balances the 0.6 log defect of the right eye. When darkest stimuli do not attenuate light 100%, calculations get more complicated since a defect dims both the top and bottom viewed stimuli on the side of the defect, the endpoint occurs when the sum of the light attenuation of the defect plus the total light attenuation of the top rivalrous fused images, 450*a*-454*a* images, divided by interocular brightness difference in log units equals the same calculations for the stimuli of the bottom rivalrous fused images, 450*b*-459*b* images.

Figure 19:
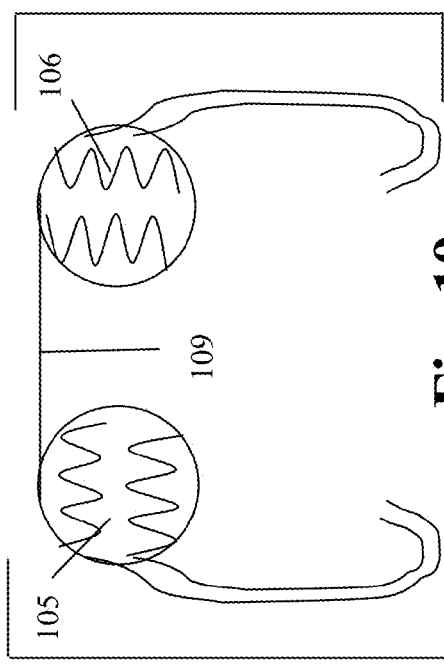
FIG. 19. Rear view of spectacles 109 holding complementary color filters
Figure 20:
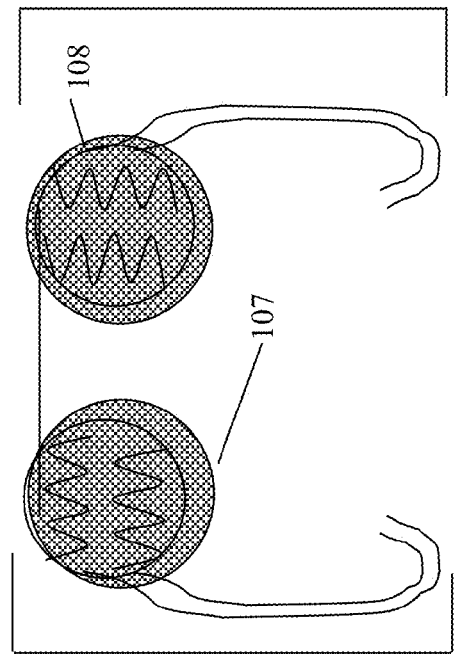
FIG. 20. Rear view of spectacles 109 holding complementary color filters and neutral density filters FIG. 21. Frontal view of computer screen 80 and fusion stimuli where binocular separation is by way of two sets of polarizing filters FIG. 22. Rear view of spectacles holding polarizing filters FIG. 23A. Comparison relatively suppressed image 86 to brighter image 87
Figure 18:
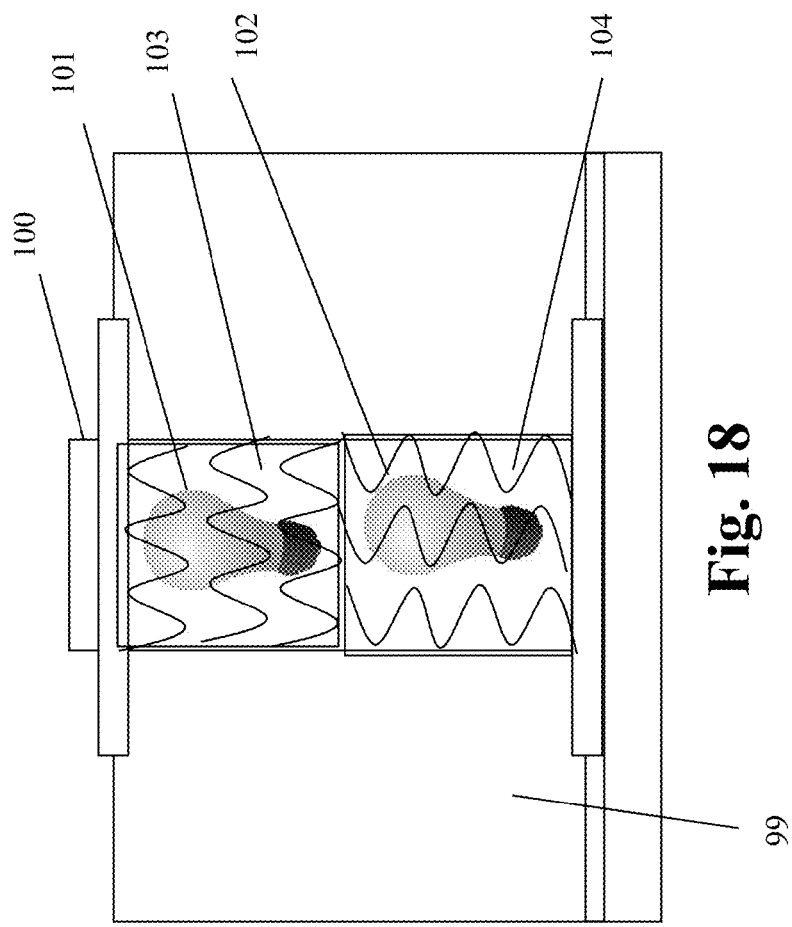
FIG. 18. Front view of computer monitor and transparent screen attachment 100 for supporting color filters 101 and 102
Figure 35:
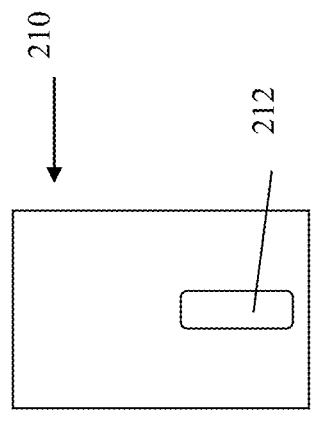
FIG. 35. Top view of top 210 showing no filters in the viewing window
Figure 37:
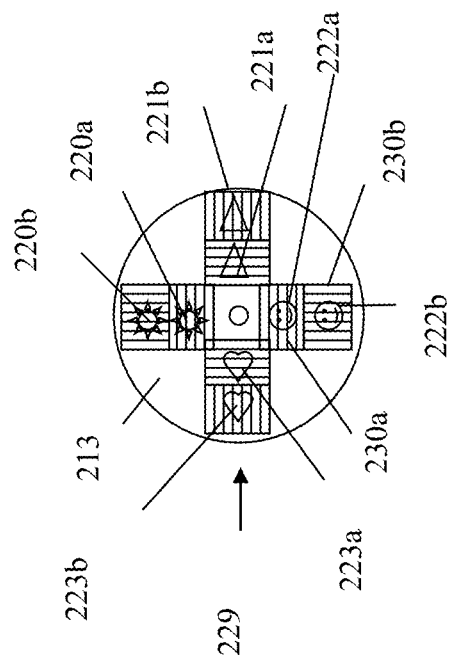
FIG. 37. Frontal view of disc 229 with stimuli covered by polarizing filters FIG. 38. Top view of hand-held viewer 231
Figure 34:
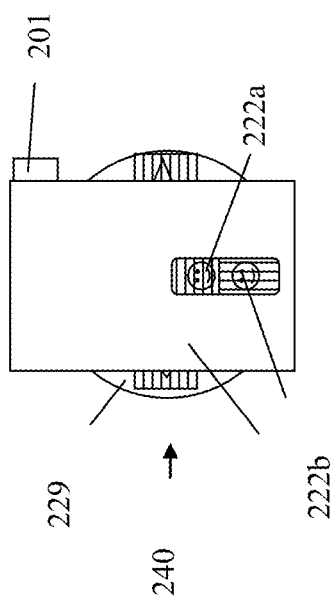
Figure 36:
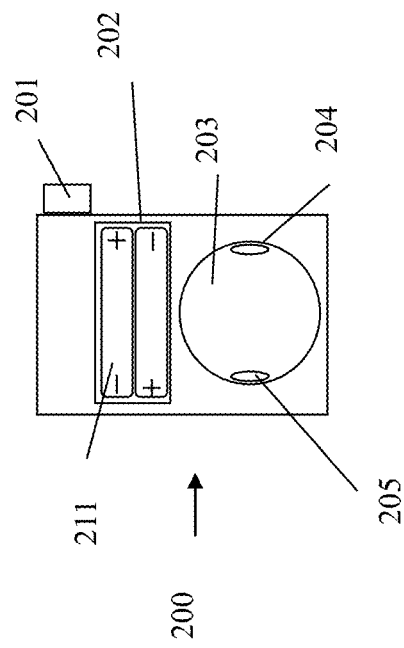
FIG. 36. Top view of base 200
Figure 42:
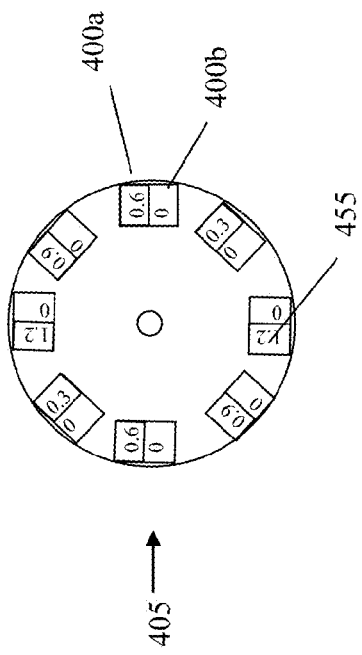

In another embodiment complementary color filters are used for binocular separation so that a rivalrous can be utilized for the benefit of detecting problems affecting the visual system. In FIG. 18 is illustrated computer screen 99, transparent screen attachment 100 for supporting color filters 103 and 104 where filters 103 and 104 are of complementary colors in that light filter 103 blocks the light in the wave lengths that pass through filter 104 and vice versa. In FIG. 19 spectacles 109 hold color filters 105 the same color as filter 103 and holds filter 106 that is the same color as filter 104. By controlling the image form, color, brightness and contrast through editing image parameters, image 101 and image 102 provide unlimited possibilities for rivalrous image combinations and the ability to change the relative brightness of images 101 and 102 to bring rivalry into balance. One method of testing is to show a series of slide where the brightness of images 101 and 102 are equal to establish if the subject has a relative afferent sensory defect. In the presence of such a defect, the image that appears dimmer is on the side of the defect. If a defect is identified, it can be quantified by presenting a series of slide in which the top or bottom image is progressively dimmed by a specific quantity. The subject advances the series until top image 101 and bottom image 102 appear the same. The subject may pass the point of equal brightness and the formerly brighter image appears to be the dimmer, a point called reverse suppression. By toggling back and forth through the brightness graded series a match is made, and endpoint termed neutralization. By knowing the relative attenuation of brightness when a match is made, quantifies the defect. Neutral density filters 107 and 108 illustrated FIG. 20 may be used for low light testing and for rivalrous stress testing as described earlier for the embodiment illustrated in FIG. 8. Alternative, complementary colored computer images viewed through complementary colored spectacle filters can be used for my rivalry test. The color images can be dimmed to quantify a vision defect.

In the remaining embodiments polarizing filters are used for stereo separation. Viewing two vertically aligned oppositely polarized images through oppositely polarized spectacle lenses a subject perceives two images for direct comparison to establish the functional equality of the right and left sides of the visual system. In the embodiment seen in FIGS. 21-23B, images 86 and 87 are presented on computer screen 80 and binocular separation is by way of two sets of polarizing filters. Polarizing filters 84 and 85 cover the computer screen and polarizing filters 91 and 92 are spectacle lenses. The polarities of the filters are such that only filters 84 and 91 transmit the image 86 and only filters 85 and 92 transmit the image 87. The rivalrous pairing is image 86 against the black background and image 87 against the black background. By controlling the image form, color, brightness and contrast through editing image parameters, image 86 and image 87 provide unlimited possibilities for rivalrous image combinations and the ability to change the relative brightness of images 86 and 87 to bring rivalry into balance. One method of testing is to present the subject with a series of 86 and 87 image sets where the brightness of images 86 and 87 is the same and then advance through presentation slides in which one of image set is progressively attenuated to determine if the subject can identify the image set where the brightness of images 86 and 87 is the same, indicating an absence of a relative afferent sensory defect. In the presence a defect, the image that appears dimmer is on the side of the defect. If a defect is identified, the defect is quantified by presenting two graded series of slides, one in which the top variable image is progressively dimmed and a second series where the bottom variable image is progressively dimmed. While progressing through these series, the subject finds the neutralization endpoint where images 86 and 87 appear equally bright. Advancing past this point, the formerly brighter top image or bottom image will become the dimmer image, a point called reverse suppression. By toggling back and forth through the brightness graded series suppression, neutralization and reverse suppression endpoints can be identified. In FIG. 23A is the perception of a left eye defect where image 87, the image seen with the good right eye is brighter than image 86 seen by the defective left eye. Progressing through the attenuation series, image 87 seen by the better right eye is dimmed until images 86 and 87 appear equally bright as illustrated in FIG. 23B, the point of neutralization. By further dimming the right eye, image 87 becomes dimmer than image 86 seen the left eye, the point of reverse suppression as illustrated in FIG. 23C.

Another embodiment illustrated in FIG. 24A is a computerized picture viewer for presenting rivalrous images. Image separation is by way of polarizing filters covering viewing screen 120. The polarity of polarizing filter 110 covering images 114, 116 and 115 is oriented 90 degrees from polarizing filter 111 covering images 113, 117, and 112. Spectacles 123 in FIG. 25 holds filter 121 having polarizing axis orientated vertically to transmit images passing through filter 111 and to block images passing through filter 110. Polarizing axis of filter 122 is orientated horizontally to transmit images passing through filter 110 and to block images passing through 111. Strips 118 and 119 serve to hold filters 110 and 111 in position and assist in maintaining fusion for subjects prone to double vision when binoculars clues are reduced. By controlling image form, color, brightness and contrast through editing image parameters, images 112-117 provide unlimited possibilities for rivalry. Neutral density filters 124a and 124b illustrated in FIG. 26 by spectacles 125 may be used for low light testing and when used monocularly provides means for rivalrous stress testing as described above. One method of testing is to maintain images 116 and 117 identical and if images 116 and 117 appear different to the subject wearing glasses shown in FIG. 25, a relative afferent defect is identified. A series of images is then presented to the subject where the brightness difference between images 113 and 114 and the brightness difference between images 112 and 115 will vary from 0% to 100% during which the subject is asked to identify the brighter image of each presented image pair. By presenting this series of images of graded brightness differences, the size of the relative afferent sensory defect is quantified. Alternatively to a series of images of differing brightness, second polarizing filter 127 can be applied over polarizing filter 110 and second polarizing filter 128 can be applied over filter 111 to dim one image as illustrated in FIG. 24B. For example by rotating filter 128 the image beneath filter 128 is dimmed while the brightness of the image beneath filter 127 remains unchanged.

Another embodiment is illustrated in FIGS. 27 through 33 where the light and image brightness is static while cross polarizing filters change the interocular brightness disparity. Hand-held battery powered viewer 160 having housing 131, faceplate 130, windows 134 and 135, switch 133, light bulb 137, and disc 132. Behind windows 134 is polarizing filter 136 and behind window 135 is polarizing filter 137, which is orientated 90 degrees to filter 136. Between the light bulb of 137 and opening 134 and 135 in positioned transparent disc 132 that is attached by post 138 to faceplate 130. Disc 132 in FIG. 28 has areas 140, 141, 142, and 143, which may be of any color, which provides for backgrounds of different color and brightness for windows 134 and 135. Images 145a and 145b are incorporated in background area 143 to assist subjects in distinguishing the relative difference between rivalrous images. Frames 150 that fit over a subjects spectacles to provide housing for cross-polarizing stationary filters 153a and 154a, cross-polarizing rotatable cross-polarizing filters 153b and 154b, and neutral density filters 155a and 155b. Handle 152a attaches to polarizing filter 153b and handle 151a attaches to polarizing filter 154b. By rotating handle 152a, polarizing filter 153b rotates while polarizing filter 153a remains stationary; this changes the angle of polarization between two polarizing filters and attenuates light with the amount of light attenuation related to the degrees of rotation. This same relationship exists between filters 154a and 154b on the opposite side and by rotating 154b in relationship to 154a, light is attenuated to the right eye. Children and adults have very different interpupillary distances. To accommodate for different interpupillary distances are clips 170 and 171 that attach to frames 169 by arms 172 and 173 as shown in FIG. 31. The selection of holes in frame 160 for mounting clips 170 and 171 depends upon the desired distance between clips to accommodate to the interpupillary distance of the subject. Selecting holes 175a and 175b provides for a wide interpupillary distance while selecting holes 174a and 174b provides for a narrow interpupillary distance. Clip 170 in FIGS. 32 and 33 is composed of lens 180, lens hinge 182, faceplate 181 with markings 184 to indicate the level of light attenuation, and cross polarizing filters 183 and 187. In FIG. 33 is cross sectional view of filter 170 showing cross polarizing filters 187 and 183, faceplate 181, rear plate 189, cushion 185, and back plate 186. Cushion 185 fits between back plate 186 and polarizing filter 183 to provide friction to maintain filter 183 fixed in a set position. Polarizing filter 187 is sandwiched between faceplate 181 and back plate 189. Cross polarizing filters 183 and 187 are aligned for full light transmission when filter 183 is aligned horizontally as illustrated in FIG. 32.

Another embodiment is illustrated in FIGS. 34 through 37 where the image brightness is varied and each image is covered by a polarizing filter and viewed through polarizing spectacles such as spectacles 123 in FIG. 25. Hand-held viewer 240 consists of base 200, top 210, and disc 229. The base illustrated in FIG. 36 had light bulbs 205 and 204 illuminating concave bowl 203, switch 201, batteries 211, and battery compartment 202. Top 210 in FIG. 35 has viewing window 212. Transparent disc 229 in FIG. 37 has eight images 220a-223b, polarizing filter 230a mounted over images 220a, 221a, 222a, and 223a and polarizing filter 230b mounted over images 220b, 221b, 222b, and 223b. Polarizing filters 230a and 230b are aligned 90 degrees to each other, such that, when a subject is wearing polarizing lenses of the same polarity as filters 230a and 230b, binocularity is separated, one eye sees primarily images 220a to 223a and the other eye primarily sees image 220b to 223b.

Yet another embodiment is illustrated in FIGS. 38 through 40. Viewer 231 having base 200 illustrated in FIG. 36 and top 232 illustrated in FIG. 39. Top 232 has polarizing filters 233a and 233b mount in the viewing window. The polarizing axis of polarizing filters 233a and 233b are aligned 90 to each other, such that, when a subject is wearing polarizing lenses of the same polarity as filters 233a and 233b, binocularity is separated, one eye sees primarily images 251a-257a and the other eye primarily sees image 251b-257b of disc 235. Top 232 allows using one set of polarizing filters, filters 233a and 233b, for the viewing entire image series on disc 235 and provided for means to quantify a defect in the visual system by viewing image pairs having different levels of brightness. For example, bottom images, 250a, 251a, 252a, 253a, 254a, 255a, 256a, and 257a form a series of progressively dim images and all top images, 250b, 251b, 252b, 253b, 254b, 255b, 256b, and 257b are of full brightness. When the polarizing glasses are aligned such that the right eye primarily views the top image a defect in the right eye is measured by rotating disc 235 counterclockwise, which progressively dims the bottom image seen by the left eye. Inverting viewer 231 a defect in the left eye is measured since the right eye is now viewing the bottom dimmer images as disc 235 is rotated counterclockwise.

My preferred embodiment is illustrated in FIGS. 41 through 48. Viewer 403 consists of back 200, disc 405, and faceplate 401. Faceplate 401 with horizontally oriented polarizing filter 406 covering the nose opening of clown 404 and with vertically oriented polarizing filter 407 covering the mouth of the clown 404. Clown 404 serves as a background for identifying the endpoint by asking, "which is brighter the nose or the mouth of the clown." Other background images may be substituted for clown 404. Disc 405 in FIG. 42 has a series of eight sets of vertically aligned rivalrous stimuli made up of (1) top stimulus 400a appearing in the nose opening of clown 404 and (2) bottom stimulus 400b appearing in the mouth opening of clown 404. For four sets, the top stimulus does not attenuate light (indicated by 0 log attenuation) and the bottom stimulus attenuates light, the amount (indicated by the 0.3 to 1.2 log units appearing within the stimulus) and for the other four set the top stimulus attenuates light and the bottom stimulus does not attenuate light. Light attenuation is in 0.3 log unit increments and the scale in this example is from 0.3 to 1.2 log units. While wearing spectacles 125, images viewed through filter 406 (clown's nose) by subject's left eye through filter 121 and images viewed through filter 407 (clown's mouth) by subject's right eye appears black while images viewed through filter 406 (clown's nose) by subject's right eye through filter 122 and images viewed through filter 407 by subjects left eye through filter 121 appear the brightness of the stimuli on disc 405. Turn to FIG. 41 to see how a 0.6 filter imbalances rivalrous fusion. When stimulus 400a of 0.6 log attenuation is in position of filter 406 (clown's nose) it appears as black image 420a to the left eye and as 0.6 log attenuated image 420c to the right eye while unattenuated stimulus 400b positioned through filter 407 (clown's mouth) appears as bright 420b image to the left eye and as black image 420d to the right eye. When the brain fuses images 420a with 420c to form perception 421a and images 420b with 420d to form perception 412b, perception 421b appears brighter than 421a.

Figure 43:
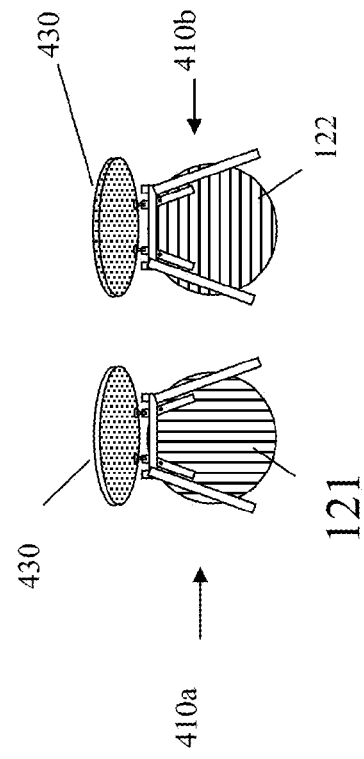
Figure 41:
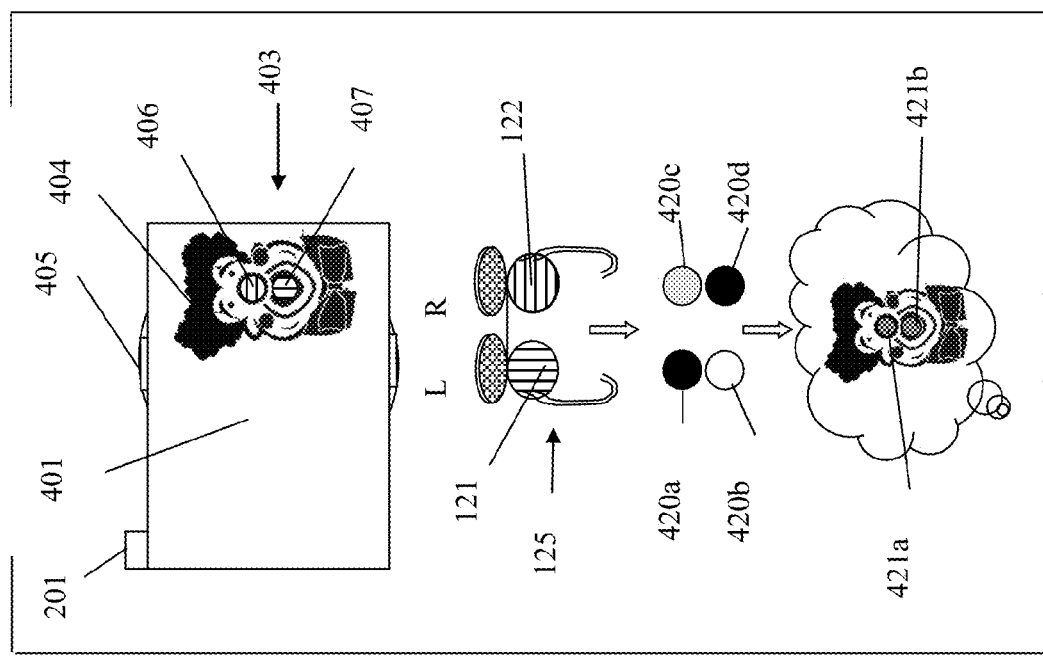
FIG. 41. Schematic showing the effect of imposed 0.6 log density imbalance perception FIG. 42. Frontal view of disc with series of stimuli from 0 log to 1.2 log density FIG. 43. Rear view of clips holding polarizing filters and neutral density filters FIG. 44. Schematic illustrating neutralizing a right eye 0.3 log defect FIG. 45. Schematic illustrating the effect of 0.9 log density left eye stress test FIG. 46. Schematic illustrating the effect of 0.9 log density right stress test FIG. 47. Illustration the easy to use score sheet

In FIG. 43 are lens clips 410a with vertically oriented polarizing filter 121 that attaches to the right lens of spectacles and 410b with horizontally oriented polarizing filter 122 that attaches to the left lens of spectacles. Neutral density filter 430 that is foldable attaches to lens clip 410a and 410b and is used for attenuating the light to one or both eyes. Benefits of the lens clips are (1) that they can be placed over the subject's prescription lenses or spectacles with blank lenses and (2) they can be easily positioned to accommodate any interpupillary distance, from the narrow interpupillary distance of a child to the wide interpupillary distance of an adult.

Figure 45:
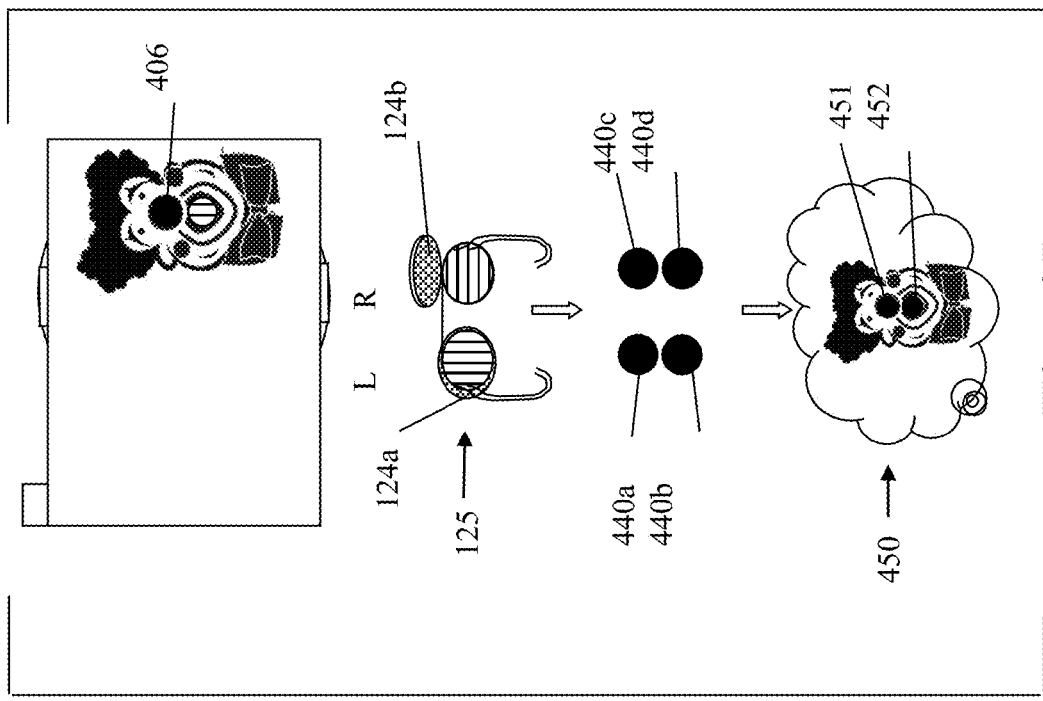
Figure 44:
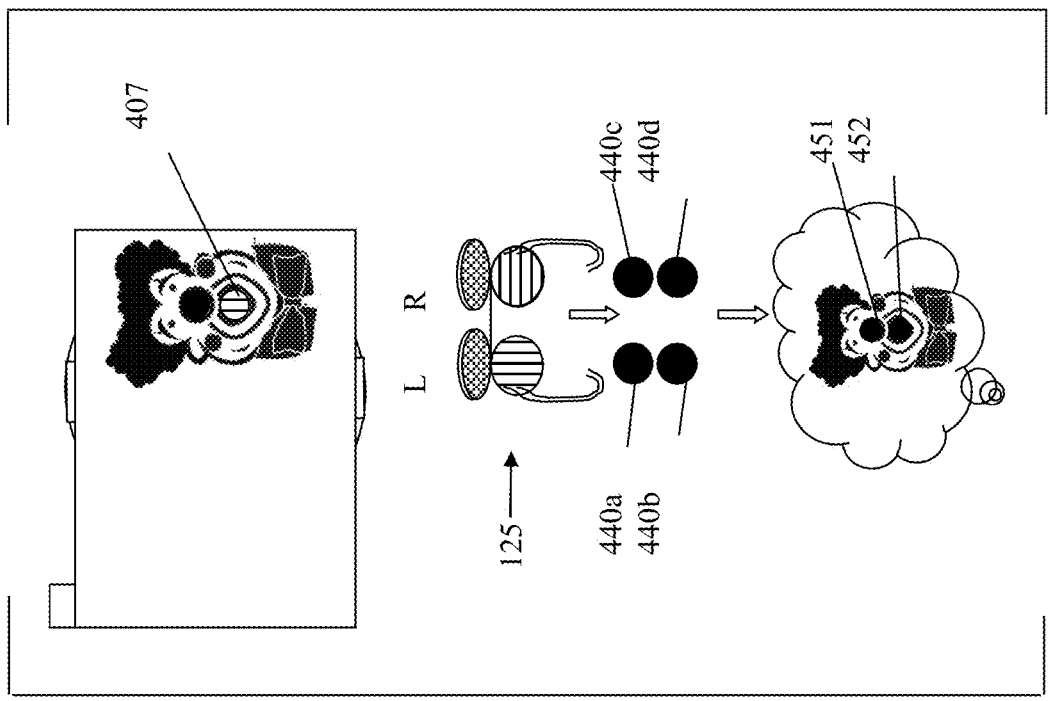
Figure 46:
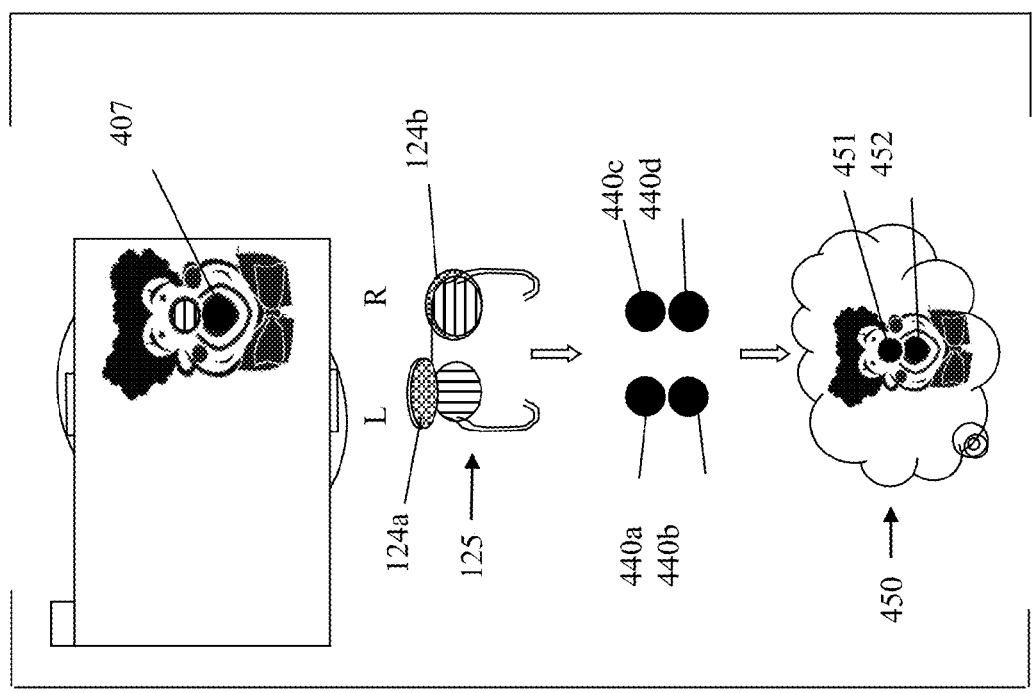

The method of testing is very easy and will be described in FIGS. 44-47 by using the example of a 0.3 log defect in the right eye of a subject. In the presence of a 0.3 defect in the right eye, the mouth appears mistakenly brighter and neutralization occurs when disc 405 is aligned with the 0.3 log attenuated stimulus in the position of the clown's mouth 407 and perception 451 and 452 appear equally bright shown in FIG. 44. For other stimuli, either the clown's nose or mouth appears appropriately brighter as indicated on the sheet of FIG. 47. To confirm the endpoint the stress test is performed while imposes an interocular brightness disparity by imposing a light attenuation filter to one eye, in this example a 0.9 log attenuating filter. The stress test amplifies a defect by doubling the magnitude of the defect. In FIG. 45 foldable 0.9 log neutral density filter 124a is placed before the left eye the subject which creates an interocular imbalance of 0.9 log left eye filter versus 0.3 log defect right eye, a net of 0.6 log brightness reduction in the left eye which is neutralized by a 0.6 log stimulus in position of polarizing filter 406 in the clown's nose which adds 0.6 log attenuation to the 0.3 log defect in the right eye. Attenuation of images passing through the lenses of spectacles 125 are black 440a 100% attenuation; dark grey 440b 1.2 log attenuation by stimulus 455 on disc 405, grey 440c 0.9 log attenuation by filter 124b, and black 440d 100% attenuation. Perceptions 451 and 452 appear equal as a result of filer 124a of 0.9 log attenuation to the left eye balanced against 0.6 log attenuation of stimulus 400a eye plus 0.3 log defect right eye. In FIG. 46 is the second part of the stress test where brightness disparity is reversed and filter 124b of 0.9 log units is lowered over the right eye which creates an interocular disparity of 1.2 log units, the 0.9 log 124b filter plus 0.3 log defect right eye against zero attenuation in the left eye. The 1.2 log disparity is balanced by a stimulus under filter 407 at the clown's mouth that attenuates brightness by 1.2 log units to the left eye. Attenuation of images passing through the lenses of spectacles 125 are black 440a 100% attenuation; grey 440b 1.2 log attenuation by filter stimulus 455 of disc 405, 440c 0.9 log attenuation by filter 124b, and black 440d 100% attenuation. Perceptions 451 and 452 appear equal as a result 1.2 log stimulus balancing the 0.9 log 124b filter and the 0.3 log density of the defect in the right eye. The stress doubled the defect in that to neutralize the 0.9 log 124a filter imposed to the left eye 0.6 log attenuating stimulus 400a was need but to neutralize 0.9 log filter 124b imposed to the right eye required 1.2 log stimulus 455. The difference in magnitude of the stimuli to neutralize an imposed 0.9 log attenuation filter is the presence of a defect is twice the magnitude as the defect.

Figure 47:
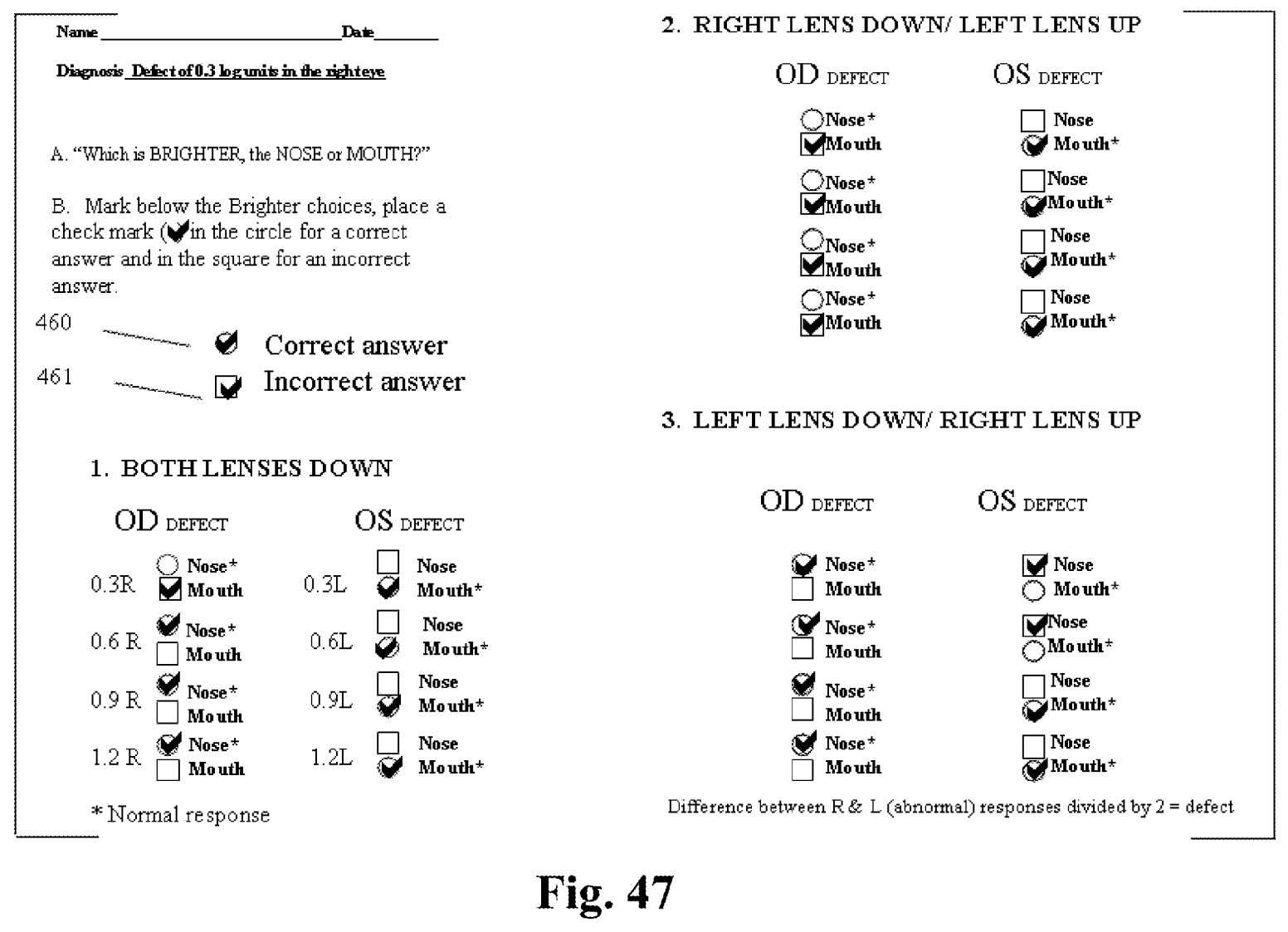

The score sheet in FIG. 47 illustrated the testing sequence and a simple method to tabulate the test results. First the test is performed with filters both 124a and 124b lowered, then the test is repeated with right 124a filter down and 124b filter raised and then with left 124b filter down and 124a filter raised. A check mark is placed in circle 460 when the subject gives a correct answer and in square 461 when the subject gives an incorrect answer. As way of illustration, the check marks in FIG. 47 is for a subject with a 0.3 log defect in the right eye, with both filters down, a right eye defect of 0.3 log units is recorded by a check mark in square 463 when the mouth appeared brighter than the nose. With the 0.9 log 124a filter over the right eye, the mouth appears brighter than the nose for 0.3 log through 1.2 log stimuli because the defect of 0.3 log plus 0.9 log of the filter gives 1.2 log interocular disparity. Now with 0.9 filter 124b over the left eye, the interocular disparity is 0.6 log units (0.9 log filter left minus 0.3 log defect right) and is neutralized by the 0.6 log stimulus over the right eye. The difference between the neutralization endpoints for dimming the right eye versus the left eye is 0.6 log unit, twice the size of the defect.

The invention claimed is:

1. A method for detecting and measuring vision defects comprising:
   a. arranging four stimuli into two fusible rivalrous image pairs where the two stimuli in each of said two fusible rivalrous image pairs are aligned horizontally and where said two fusible rivalrous image pairs vertically forming a top rivalrous pair and a bottom rivalrous pair that appear as a single top image and a single bottom image when fused by a subject,
   b. creating reciprocal brightness of said two fusible rivalrous pairs where each of said two fusible rivalrous pair has a bright and a dim image, where the left image of said top rivalrous pair is equally bright as the right image of said bottom rivalrous pair and the right image of said top rivalrous pair is equally bright as the left image of said bottom rivalrous pair,
   c. presenting one member of each of said two fusible rivalrous image pairs to the right eye and the opposite member of said two fusible rivalrous image pairs to the left eye, and
   d. varying the brightness of a least one image in said two fusible rivalrous image pairs to achieve the equality endpoint the point when said single top image appears equal to said single bottom image.

2. The method of claim 1 wherein varying the brightness of a least one of said four stimuli is by adjusting the brightness of the light source to one eye by imposing one or more neutral density or cross polarizing filter before one eye, or by changing the contrast or brightness of the at lease one of said four stimuli viewed in a stereoscope or in a computer-generated per viewable on a monitor,
   Whereby, the brightness of each side of the visual system, can be adjusted to achieve equality of apparent brightness of said single top image and said single bottom image and the identification and quantification of a possible defect.

3. The method of claim 1 where presenting binocular separation of members of said two fusible rivalrous image pairs to the right and left eyes is with polarizing filter or complementary color filter techniques.

4. The method of claim 1 where binocular separation of members of said two fusible rivalrous image, pairs is a hand-held stereoscope where the illumination of said stimuli on the right and left side of the subject are independently adjustable.

5. The method of claim 1 wherein said equality endpoint is compared after imposing a neutral density over the right eye of the subject to after imposing said neutral density filter over the left eye of said subject, whereby, the difference between said endpoints resulting from right-left monocular dimming amplifies a brightness sense imbalance.

6. A device for measuring the relative vision function comprising:
   a. a computer monitor capable of receiving programmable computer-generated input,
   b. four computer-generated stimuli forming two fusible rivalrous image pairs where the two stimuli in each of said two fusible rivalrous image pairs are aligned horizontally and where said two fusible rivalrous image pairs are aligned vertically forming a top rivalrous pair and a bottom rivalrous pair that appear as a single top image and a single bottom image when fused by a subject,
   c. images of reciprocal brightness forming fusible rivalrous pairs where each of said two fusible rivalrous pair has a bright and a dim image, where the left image of said top rivalrous pair is equally bright as the right image of said bottom rivalrous pair and the right image of said top rivalrous pair is equally bright as the left image of said bottom rivalrous pair,
   d. stereoscopic separating techniques comprising polarizing right-left glasses in conjunction with paired polarizing filters over said computer monitor, complementary right-left color glasses paired with complementary filters over said computer monitor for binocular separation of subject's vision, or a physical stereoscopic divider to block the right eye from seeing the left sided images and the left eye from seeing the right sided images, and
   e. computer-generated input for changing the brightness of at least one of said four stimuli,
   whereby imbalance of the brightness sense between right and left sides of the subject's visual system can be identified and quantified by selectively dimming at least one of said four stimuli viewed by the better eye.

7. A device for measuring the relative vision function comprising:
   a. a right spectacle electronic monitors viewable by only the right eye and a left spectacle electronic monitor viewable by only the left eye of a subject,
   b. four computer-generated stimuli forming two fusible rivalrous image pairs where the two stimuli in each of said two fusible rivalrous image pairs are aligned horizontally and where said two fusible rivalrous image pairs are aligned vertically forming a top rivalrous pair and a bottom rivalrous pair that appear as a single top image and a single bottom image when fused by a subject,
   c. reciprocal brightness of said two fusible rivalrous pairs where each of said two fusible rivalrous pair has a bright and a dim image, where the left image of said top rivalrous pair is equally bright as the right image of said bottom rivalrous pair and the right image of said top rivalrous pit i equally bright as the left image of said bottom rivalrous pair, and d. computer input to each of said spectacle monitors capable of programming color, form, image sequencing, and changing the brightness of a least one image in said two fusible rivalrous image pairs to achieve the equality endpoint, the point when said single top image appears equal to said single bottom image.

8. A device of claim 7 wherein changing the interocular brightness is by attenuating the brightness of said right monitor in comparison to said left monitor or by attenuating the brightness of said left monitor in comparison to said right monitor.

9. The device of claim 7 wherein multiple pairs of said two fusible rivalrous image pairs are sequentially presented in a series where the right-left reciprocal brightness of two fusible rivalrous image pairs is progressively made unequal by reducing, the brighter stimulus viewed in said right monitor and followed by multiple pairs of two fusible rivalrous image pairs sequentially re ent right-left reciprocal brightness of the said rivalrous pairs is progressively made unequal by reducing the brighter stimulus viewed in said, left monitor to achieve the equality endpoint the point when said single top image appears equal to said single bottom image.

\* \* \* \* \*